(12) United States Patent
Takemoto

(10) Patent No.: US 8,784,299 B2
(45) Date of Patent: Jul. 22, 2014

(54) OPERATION MECHANISM, ENDOSCOPE APPARATUS, AND GUIDE CATHETER

(75) Inventor: Shotaro Takemoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 26 days.

(21) Appl. No.: 13/284,060

(22) Filed: Oct. 28, 2011

(65) Prior Publication Data

US 2012/0302949 A1 Nov. 29, 2012

Related U.S. Application Data

(63) Continuation of application No. PCT/JP2011/060453, filed on Apr. 28, 2011.

(60) Provisional application No. 61/328,814, filed on Apr. 28, 2010, provisional application No. 61/353,805, filed on Jun. 11, 2010.

(51) Int. Cl.
*A61B 1/00* (2006.01)
*A61M 31/00* (2006.01)

(52) U.S. Cl.
CPC .............. *A61B 1/00* (2013.01); *A61B 1/00147* (2013.01)
USPC .......................... 600/104; 600/146; 604/95.04

(58) Field of Classification Search
USPC .......................... 600/104, 139, 141, 146, 147; 604/95.01, 95.04
See application file for complete search history.

(56) References Cited

U.S. PATENT DOCUMENTS

| 2006/0189845 A1* | 8/2006 | Maahs et al. ................. 600/146 |
| 2008/0103520 A1* | 5/2008 | Selkee ........................ 606/195 |
| 2009/0234280 A1 | 9/2009 | Tah et al. |
| 2010/0004591 A1 | 1/2010 | Barenboym et al. |

FOREIGN PATENT DOCUMENTS

| JP | 51-91989 | 7/1976 |
| JP | 02-126825 A | 5/1990 |
| JP | 11-032977 A | 2/1999 |

(Continued)

OTHER PUBLICATIONS

Japanese Office Action dated Aug. 15, 2012 from corresponding Japanese Patent Application No. 2011-545121 together with English language translation.

(Continued)

*Primary Examiner* — Alireza Nia
*Assistant Examiner* — Timothy J Neal
(74) *Attorney, Agent, or Firm* — Scully, Scott, Murphy & Presser, P.C.

(57) ABSTRACT

An operation mechanism includes: a longitudinal member having a channel; a subject operation section provided at a distal end side of the member; an operation section provided at a proximal end side of the member; a first transmission means connected to the subject operation section at a distal end side thereof and formed to penetrate the operation section transmitting a first driving force; a first input portion provided in the operation section and connected to a proximal end side of the first transmission means to operate the subject operation section; a second input portion provided closer to the subject operation section side of the operation section than the first input portion and operated by a medical instrument inserted through the channel; and second transmission means connected to the first input portion and the second input portion and transmits a second driving force.

7 Claims, 16 Drawing Sheets

(56) References Cited

FOREIGN PATENT DOCUMENTS

| | | |
|---|---|---|
| JP | 2000-023908 A | 1/2000 |
| JP | 2002-136467 A | 5/2002 |
| JP | 2004-358012 A | 12/2004 |
| JP | 2005-168882 A | 6/2005 |
| JP | 2007-190047 A | 8/2007 |
| JP | 2009-160211 A | 7/2009 |
| JP | 2009-195694 A | 9/2009 |
| WO | WO 2006/126265 A1 | 11/2006 |

OTHER PUBLICATIONS

European Search Report dated Oct. 22, 2012 from corresponding European Patent Application No. EP 11 77 5147.9.
International Search Report PCT/JP2011/060453 dated Jun. 28, 2011, together with English language translation.

* cited by examiner

OPERATION MECHANISM, ENDOSCOPE APPARATUS, AND GUIDE CATHETER

This application is a Continuation of International Application No. PCT/JP2011/060453 filed on Apr. 28, 2011 claiming priority based on U.S. Patent Application No. 61/328,814 filed on Apr. 28, 2010 and U.S. Patent Application No. 61/353,805 filed on Jun. 11, 2010, the content of which is incorporated herein by reference.

BACKGROUND OF THE INVENTION

1. Field of the Invention

The present invention relates to an operation mechanism, an endoscope apparatus, a medical device, and a guide catheter.

2. Description of Related Art

Hitherto, an endoscope apparatus has been used in order to observe and treat a treatment subject portion or the like inside a body cavity. There is a known endoscope apparatus in which a flexible elongated insertion section that is inserted into a body cavity is connected to an operation section that is used to operate the insertion section (for example, see Japanese Patent Application, First Publication No. 2005-168882). Further, Japanese Patent Application, First Publication No. 2004-358012 discloses an endoscope operation section which allows an operator who operates the endoscope apparatus to be able to operate the endoscope treatment instrument and the endoscope apparatus without an assistant.

Further, hitherto, as a medical device equipped with a curved portion that may be operated to be curved, there is a known medical device equipped with an operation mechanism that transmits an operation input which curves the curved portion to the curved portion. As an example of the medical device equipped with the operation mechanism, for example, International Patent Application Publication No. 2006/126265 discloses an endoscope apparatus including a ball shaft to which a wire used for curving a curved portion is connected and an operation lever which is connected to the ball shaft, wherein, when the operation lever installed on the ball shaft is tilted down so as to pull the wire, the curved portion is curved.

Further, Japanese Patent Application, First Publication No. 2000-23908 discloses a technique in which the position of a wire is made to be offset by 45° in the circumferential direction of a curved portion with respect to the position of a rivet which connects joint portions of the curved portion of the endoscope in order to decrease the diameter of the distal end portion of the endoscope.

SUMMARY OF THE INVENTION

According to a first aspect of the invention, there is provided a medical device including: a longitudinal member that has a longitudinal axis and has a channel formed along the longitudinal axis; a subject operation section that is provided at a distal end side of the longitudinal member; a first transmission means that is connected to the subject operation section at a distal end thereof and transmits a driving force for operating the subject operation section; an operation section that is provided at a proximal end side of the longitudinal member; a first input portion that is connected to a proximal end side of the first transmission means so as to operate the subject operation section and is provided in the operation section so as to be operated with respect to the operation section; a second input portion that is provided in the operation section so as to be operated with respect to the operation section and is provided in a medical instrument to be inserted through the channel; and a second transmission means that is connected to the first input portion and the second input portion and transmits a driving force for moving the first transmission means along the longitudinal axis direction from the second input portion to the first input portion.

DETAILED DESCRIPTION OF THE INVENTION

Figure 1A:
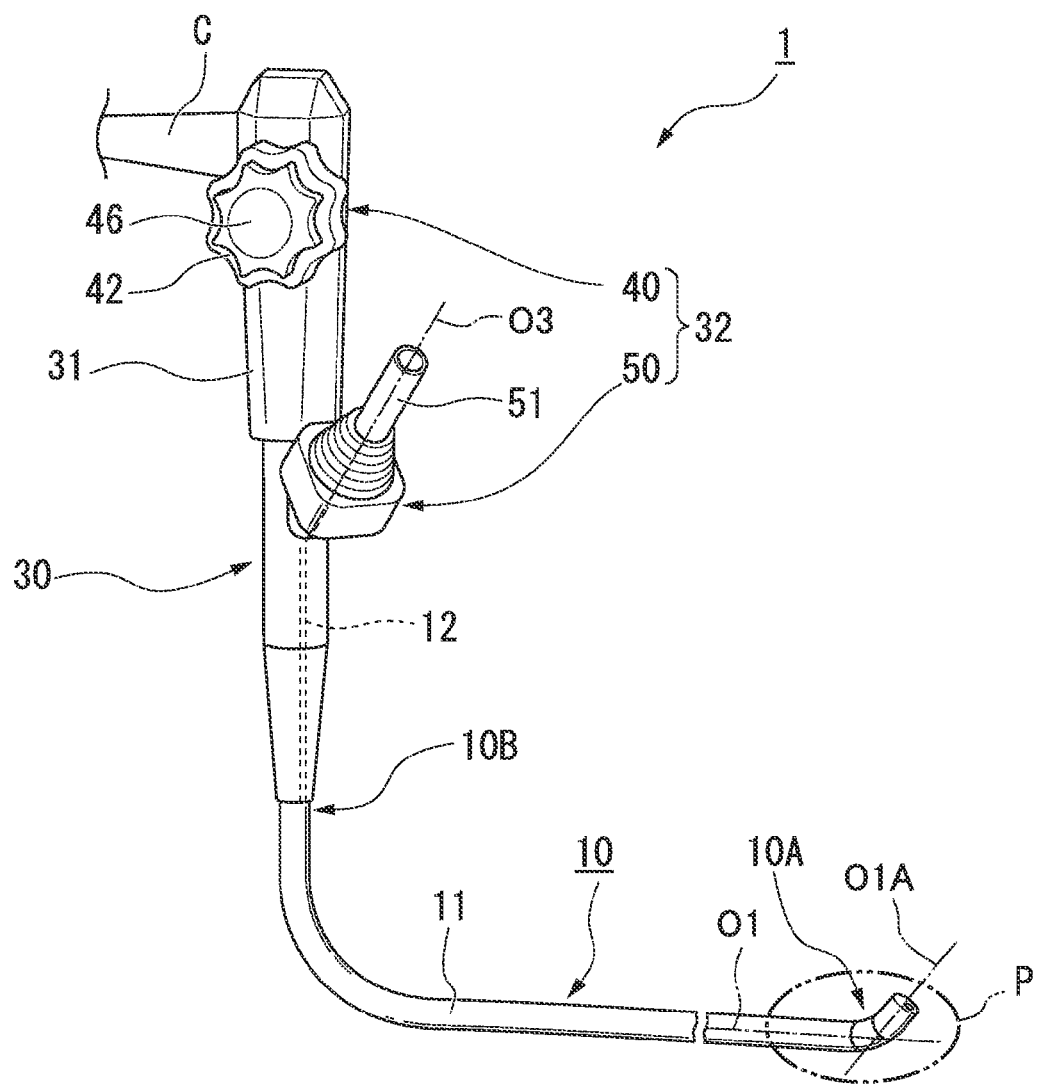
FIG. 1A is a perspective view illustrating an endoscope apparatus that includes an operation mechanism of the embodiment.
Figure 1B:
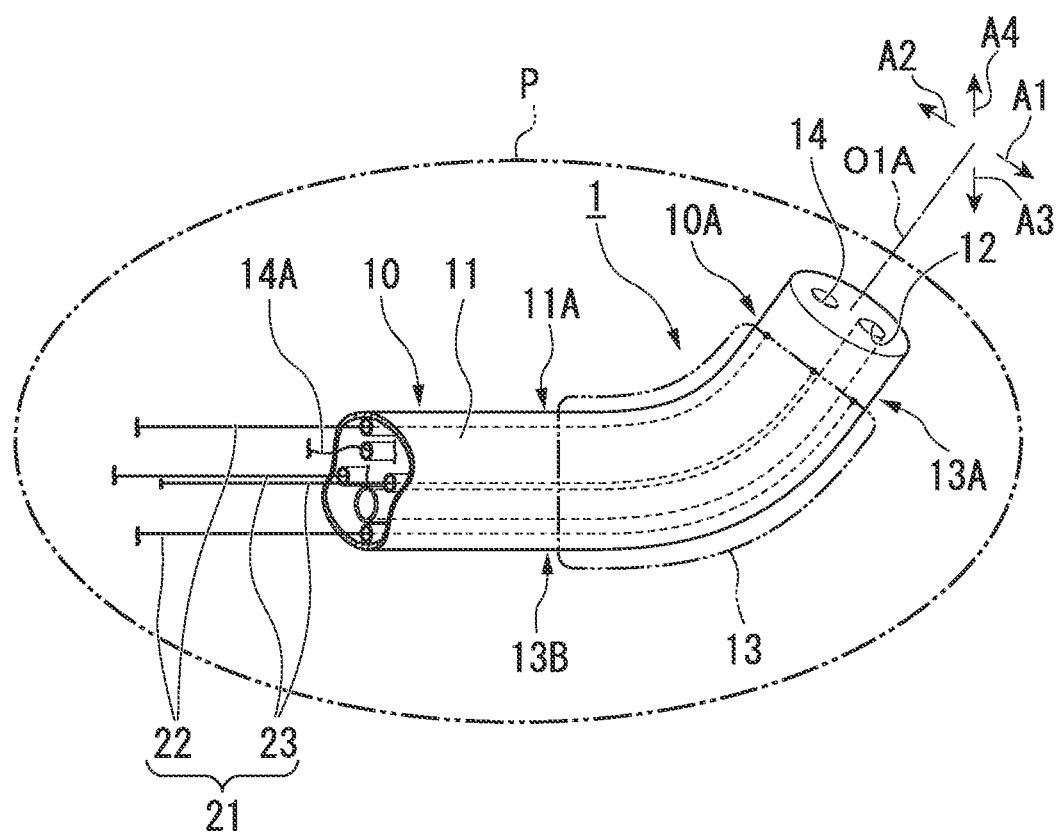
FIG. 1B is a perspective view illustrating the configuration of a part of the endoscope apparatus that includes the operation mechanism of the embodiment.
Figure 2:
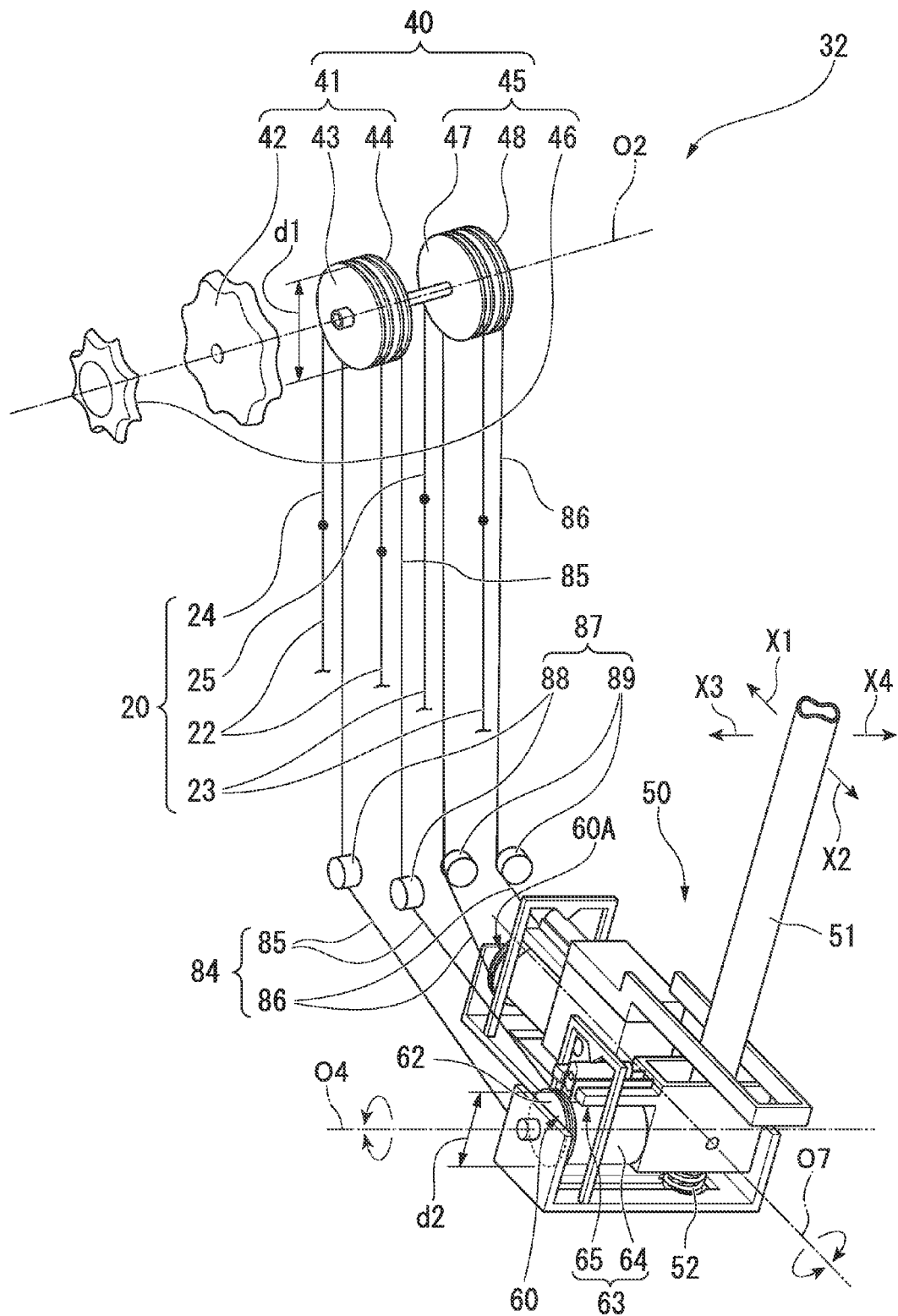
FIG. 2 is an exploded perspective view illustrating the configuration of the operation mechanism.
Figure 3:
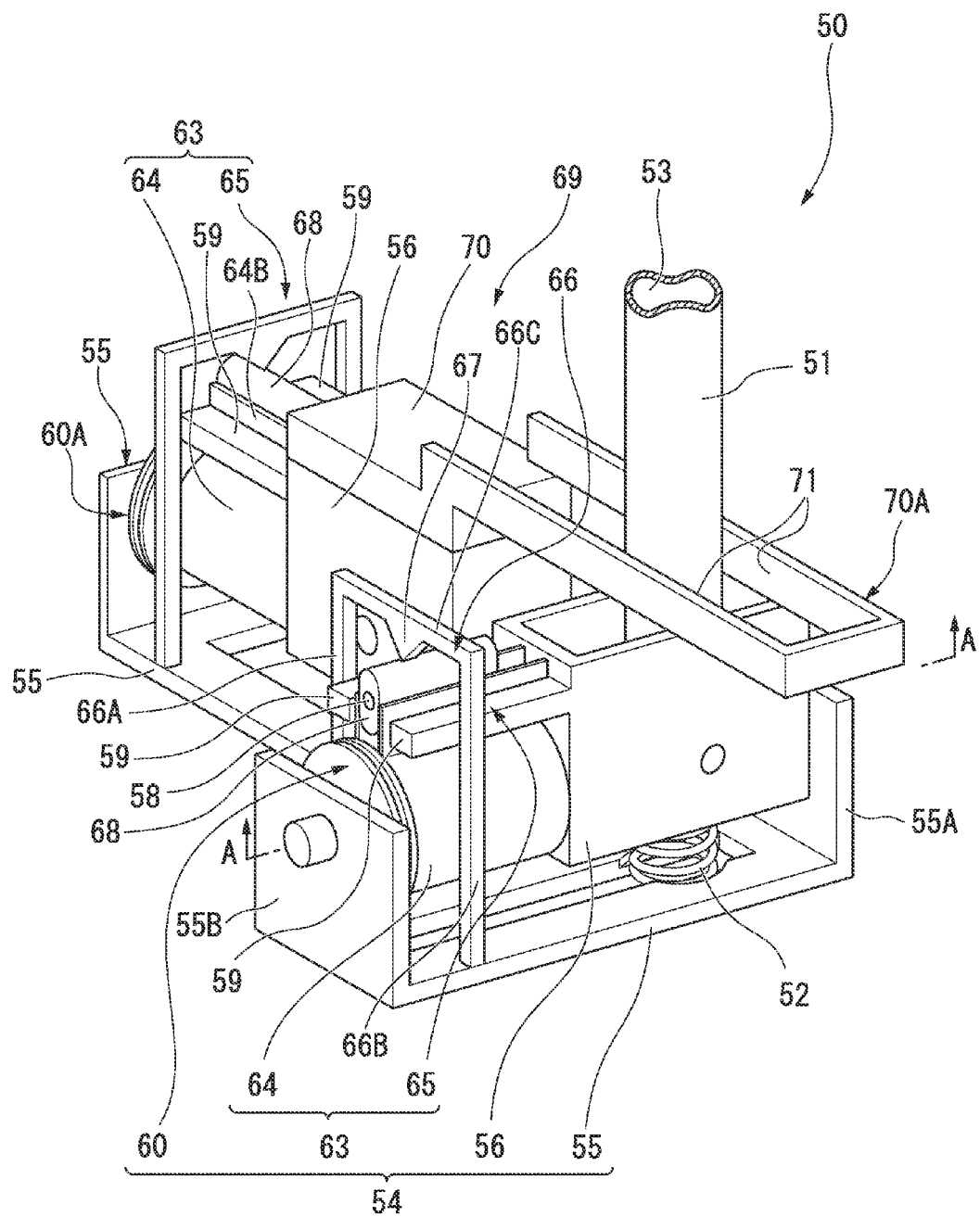
FIG. 3 is a perspective view illustrating the configuration of a tilt input portion (a second input portion) of the operation mechanism.
Figure 4:
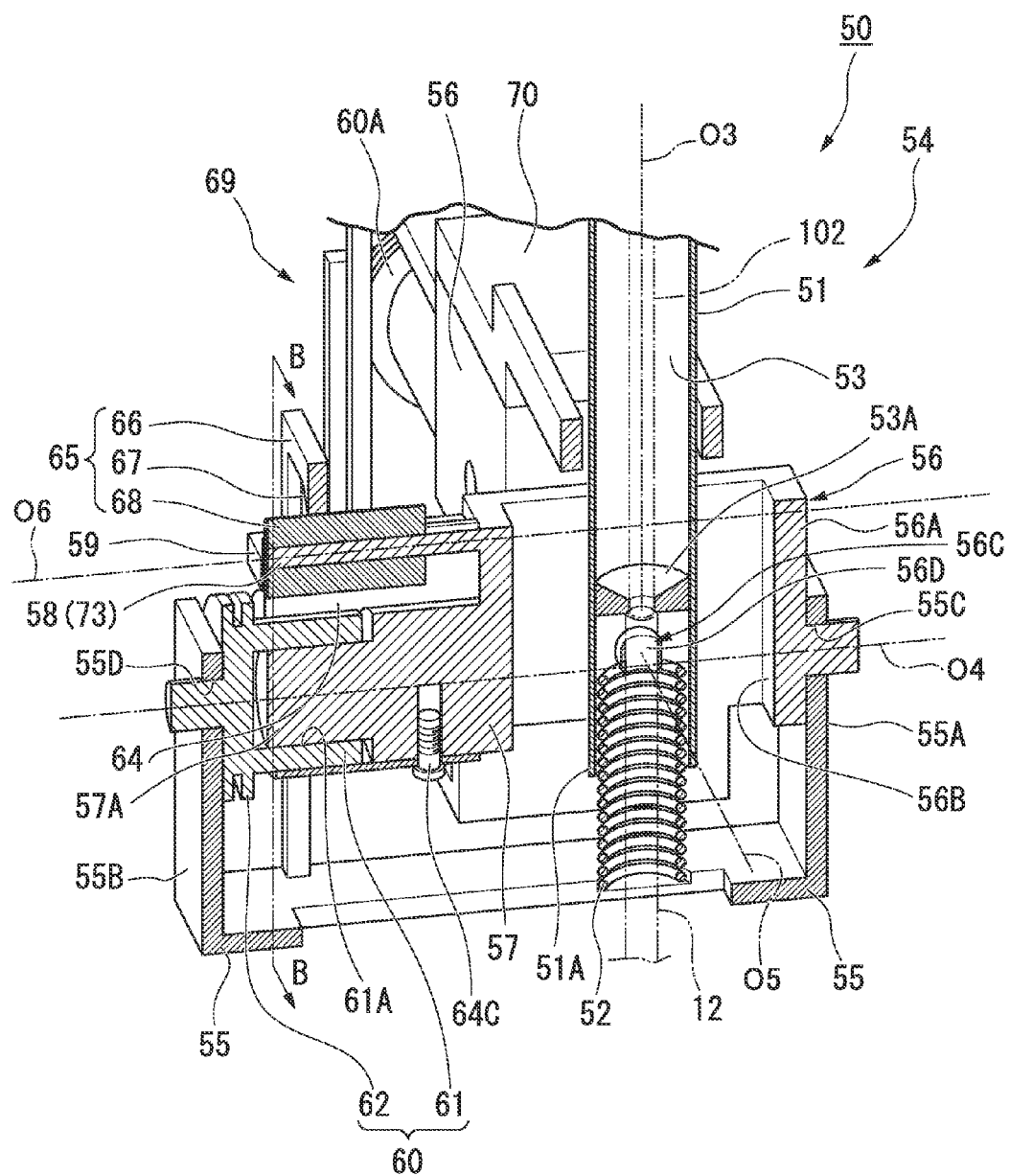
FIG. 4 is a cross-sectional view taken along the line A-A of FIG. 3, and is a diagram illustrating the configuration of a first tilting mechanism 54 of the tilt input portion.
Figure 5:
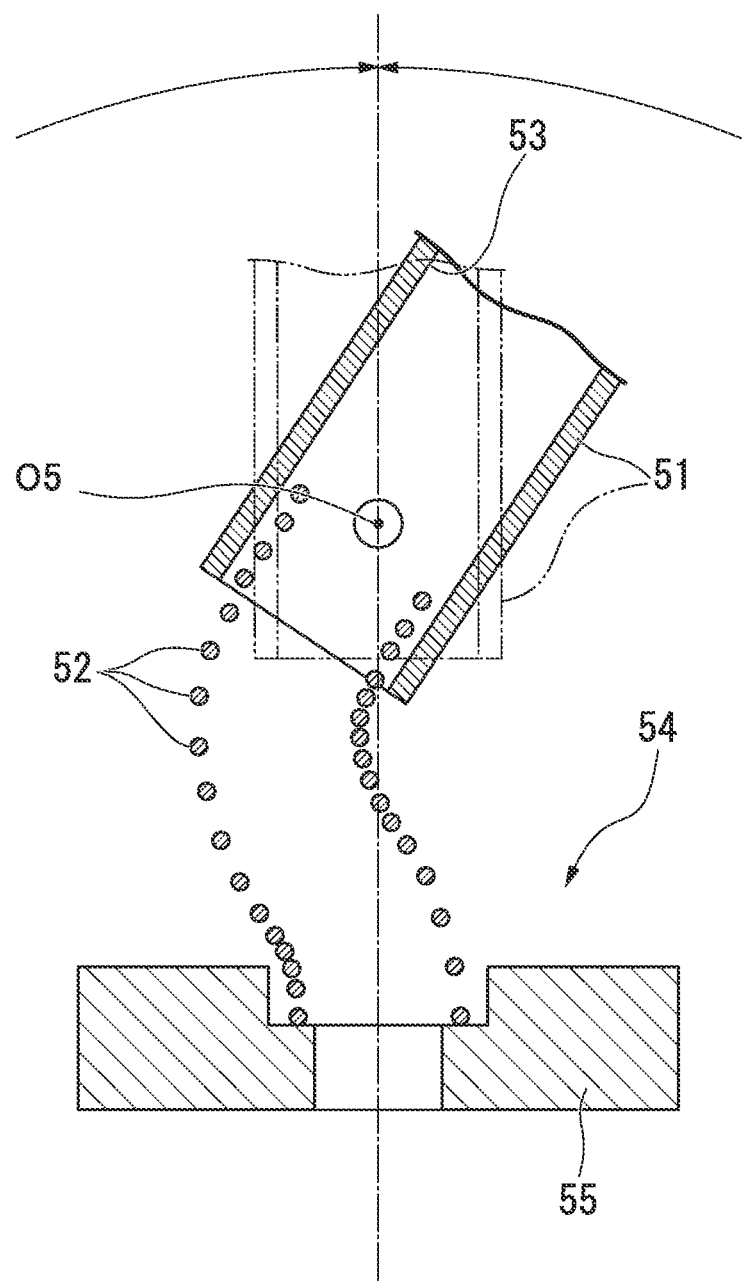
FIG. 5 is a diagram illustrating the operation of a coil spring (a neutral mechanism) in the tilt input portion.
Figure 6:
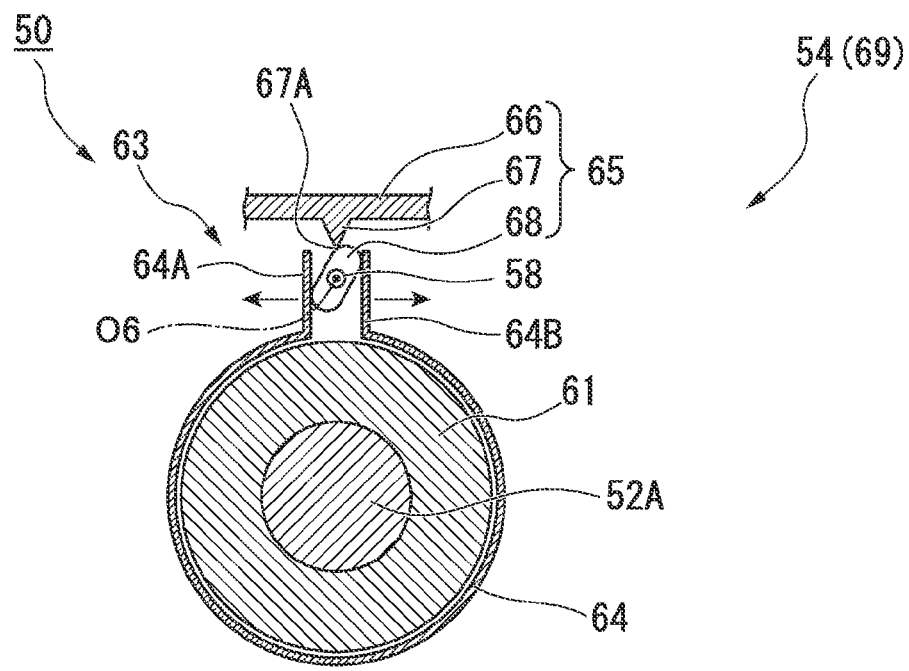
FIG. 6 is a cross-sectional view taken along the line B-B of FIG. 4, and is a diagram illustrating the operation of the tilt input portion.
Figure 7:
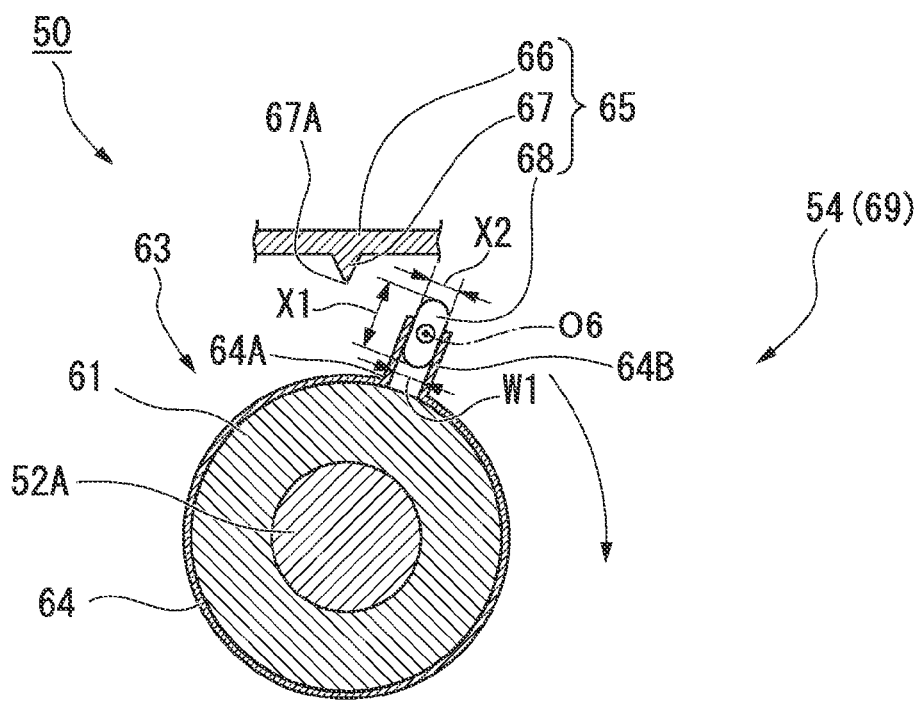
FIG. 7 is a cross-sectional view taken along the line B-B of FIG. 4, and is a diagram illustrating the operation of the tilt input portion.
Figure 8:
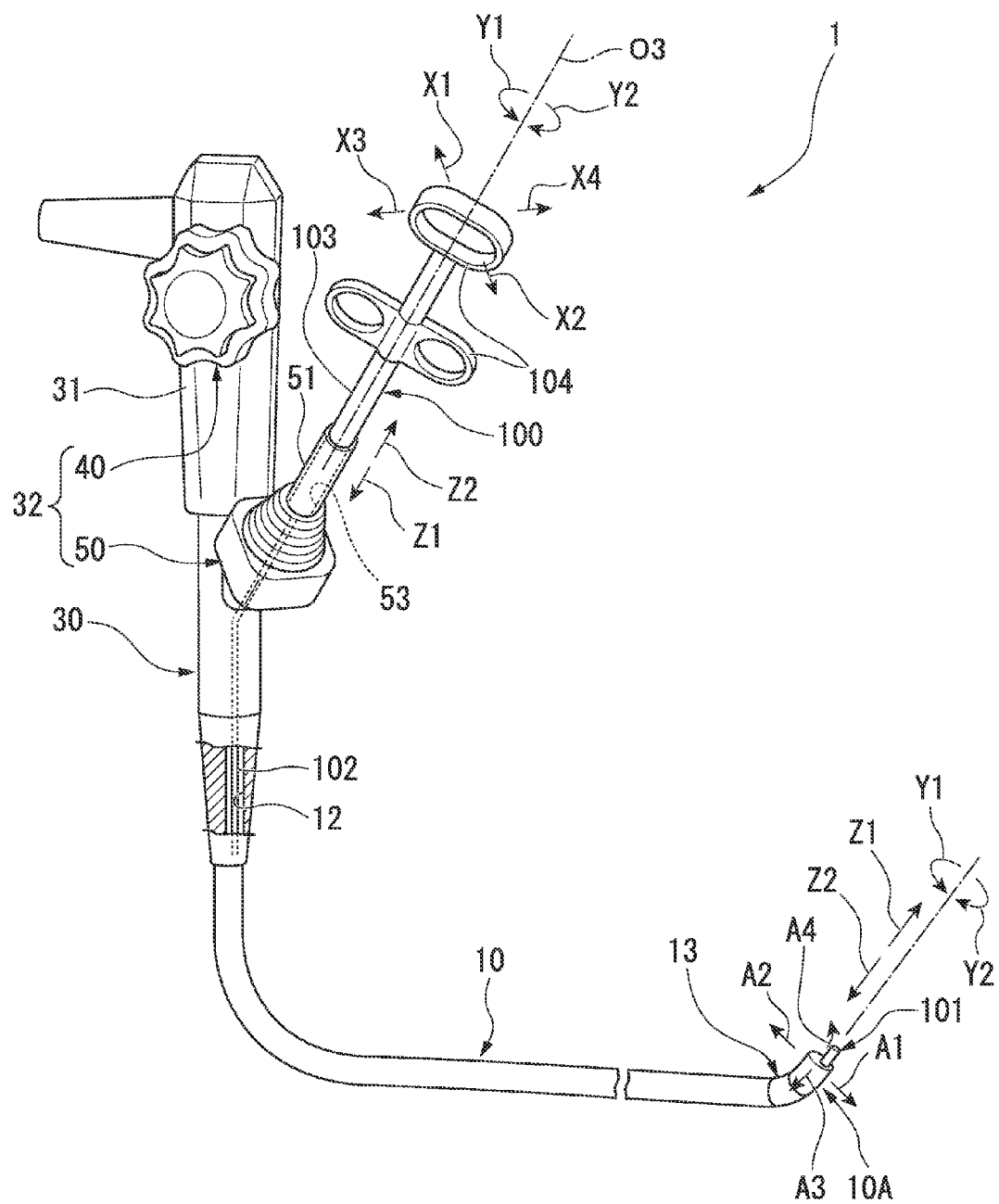
FIG. 8 is an operational diagram illustrating the operation when the endoscope apparatus is used.

An operation mechanism 32 of a first embodiment of the invention will be described together with an endoscope apparatus 1 including the operation mechanism 32 by referring to FIGS. 1A to 8. FIG. 1A is a perspective view illustrating the endoscope apparatus 1 that includes the operation mechanism 32 of the embodiment. Further, FIG. 1B is an enlarged view illustrating a part of the endoscope apparatus 1 (a part P shown in FIG. 1A). Further, FIG. 2 is an exploded perspective view illustrating the configuration of the operation mechanism 32. Further, FIG. 3 is a perspective view illustrating the configuration of a tilt input portion (a second input portion) 50 of the operation mechanism 32. Further, FIG. 4 is a cross-sectional view taken along the line A-A of FIG. 3, and is a diagram illustrating the configuration of a first tilting mechanism 54 of the tilt input portion 50. Further, FIG. 5 is a diagram illustrating the operation of a coil spring (a neutral mechanism) 52 of the tilt input portion 50. Further, FIGS. 6 and 7 are cross-sectional views taken along the line B-B of FIG. 4, and is a diagram illustrating the operation of the tilt input portion 50. Further, FIG. 8 is an operational diagram illustrating the operation when the endoscope apparatus 1 is used.

As shown in FIGS. 1A and 1B, the endoscope apparatus 1 is used to observe the inside of a body cavity, and includes an insertion section (a longitudinal member) 10 and an operation section 30.

The insertion section 10 is inserted into the body cavity from its distal end 10A. The insertion section 10 includes an insertion body 11, a curved portion (a subject operation section) 13, and an observation means 14.

The insertion body 11 is formed in a substantially cylindrical shape, and has flexibility. The inside of the insertion body 11 is provided with a cylindrical treatment instrument channel 12 which serves as an insertion path for an endoscope treatment instrument 100 (a medical instrument: see FIG. 8) performing a treatment inside the body cavity and is formed by extending from the distal end 10A of the insertion section 10 to the operation section 30, and operation wires 22 and 23 of a first transmission portion 20 to be described later.

The curved portion 13 is provided in a distal end 11A of the insertion body 11 on the side of the distal end 10A of the insertion section 10 in the insertion direction. The shape of the curved portion 13 is a cylindrical shape which communicates with the inside of the insertion body 11. When the curved portion 13 is operated to be curved, the direction of the distal end 13A with respect to a proximal end 13B of the curved portion 13 may be changed.

The observation means 14 is provided on the distal end 13A side of the curved portion 13. The observation means 14 includes, for example, a CCD or CMOS area image sensor, and captures an image in an imaging field in order to observe the inside of the body cavity. The observation means 14 is electrically connected to a signal line 14A which is inserted through the inside of the insertion body 11 and a universal cable C which is connected to the operation section 30, and an image which is obtained therefrom is displayed on a display device (not shown) which is disposed outside the body.

The operation section 30 is used to rotate the insertion section 10 about the center axis line (the longitudinal axis) O1 of the insertion section 10 or curve the curved portion 13. The operation section 30 is fixed to a proximal end 10B of the insertion section 10 in the insertion direction, and the operation section 30 is provided with a grip portion 31 and an operation mechanism 32.

The grip portion 31 is gripped by an operator of the endoscope apparatus 1. The external shape of the grip portion 31 is a substantially columnar shape which is substantially coaxial with the insertion section 10.

The operation mechanism 32 is used to curve the curved portion 13. The operation mechanism 32 includes a rotation input portion (a first input portion) 40 and a tilt input portion (a second input portion) 50.

As shown in FIG. 1B and FIG. 2, a first driving force for curving the curved portion 13 is input by rotating the rotation input portion 40 about the rotation axis O2. The rotation input portion 40 includes a first rotation input portion 41 which is used to direct the distal end 13A of the curved portion 13 toward a first direction A1 and a second direction A2 perpendicular to the center axis line O1A of the curved portion 13 with respect to the proximal end 13B of the curved portion 13 and a second rotation input portion 45 which is used to direct the distal end 13A of the curved portion 13 toward a third direction A3 and a fourth direction A4 (see FIG. 8) perpendicular to the center axis line O1A and perpendicular to the first direction A1 and the second direction A2 with respect to the proximal end 13B of the curved portion 13.

The first rotation input portion 41 includes a first angle knob 42, a disk member 43 which is coaxial with the first angle knob 42 and is attached to the first angle knob 42, and a first pulley 44 which is fixed to the disk member 43.

The first angle knob 42 rotates about the rotation axis O2. The shape of the first angle knob 42 is a substantially plate shape which follows a plane perpendicular to the rotation axis O2, and an uneven portion which prevents sliding is formed in the outer periphery thereof.

The disk member 43 has a disk shape which is formed about the rotation axis O2, and a driving wire 24 to be described later may be wound on the outer periphery thereof.

The first pulley 44 is fixed to the disk member 43 so as to be coaxial with the center (the rotation axis O2) of the disk member 43, and rotates about the rotation axis O2 along with the disk member 43. The shape of the first pulley 44 is a disk shape which is formed about the rotation axis O2. An input wire 85 to be described later may be wound on the outer periphery of the first pulley 44. In the embodiment, the pulley diameter of the first pulley 44 is equal to the pulley diameter of the disk member 43. Furthermore, the pulley diameter of the first pulley 44 may be different from the pulley diameter of the disk member 43.

The second rotation input portion 45 includes a second angle knob 46, a disk member 47 which is coaxial with the second angle knob 46 and is attached to the second angle knob 46, and a first pulley 48 which is fixed to the disk member 47.

The second angle knob 46 rotates about the rotation axis O2. The second angle knob 46 is formed in a substantially disk shape of which the diameter is smaller than the diameter of the first angle knob 42, and an uneven portion which prevents sliding is formed in the outer periphery of the second angle knob as in the first angle knob 42. Further, the second angle knob 46 and the first angle knob 42 are attached to the outer peripheral surface of the operation section 30 so as to overlap each other.

The disk member 47 is a disk-like member which is formed about the rotation axis O2 as in the disk member 43. A driving wire 25 to be described later may be wound on the outer periphery of the disk member 47.

The first pulley 48 is a disk-like member which is formed about the rotation axis O2, and an input wire 86 to be described later may be engaged to the outer periphery thereof. The outer periphery of the first pulley 48 engages with the input wire 85 through the friction therebetween. In the embodiment, the first pulley 48 is formed so as to have the same shape and size as those of the first pulley 44. Furthermore, the first pulley 48 and the first pulley 44 may have different shapes and sizes.

As shown in FIG. 3, a second driving force for curving the curved portion 13 is input by tilting the tilt input portion 50 from a predetermined neutral position (see FIG. 1B). The tilt input portion 50 includes an operation stick 51, a coil spring (a neutral mechanism) 52, a first tilting mechanism 54, and a second tilting mechanism 69.

The operation stick 51 is formed in a cylindrical shape. The size of the inner diameter of the operation stick 51 is equal to or larger than the sizes of the outer diameters of an insertion section 102 and an operation section 103 of the endoscope treatment instrument 100 (see FIG. 8). For this reason, the insertion section 102 of the endoscope treatment instrument 100 (see FIG. 8) may be inserted into the operation stick 51 and the operation section 103 of the endoscope treatment instrument 100 may be fitted thereinto. Further, the internal shape of the operation stick 51 has a circular cross-section perpendicular to the axial direction. For this reason, the operation stick 51 may rotate the operation section 103 of the endoscope treatment instrument 100 inside the operation stick 51.

As shown in FIG. 4, the operation stick 51 is disposed at a position where the insertion section 102 is not distorted with respect to the treatment instrument channel 12 when the insertion section 102 which is inserted through the inside of the operation stick 51 is inserted through the treatment instrument channel 12.

The inside of the operation stick 51 is provided with a centering member 53A which has a penetration hole coaxial with the center axis line O3 of the operation stick. A tube which forms the treatment instrument channel 12 is connected to the centering member 53A at the side facing the distal end 51A of the operation stick 51, and the penetration hole of the centering member 53A communicates with the lumen of the treatment instrument channel 12. A tapered surface which protrudes to the distal end 51A of the operation stick 51 as the surface is closer to the center axis line O3 is formed in the centering member 53A on the opposite side of the distal end 51A of the operation stick 51. Since the insertion section 102 of the endoscope treatment instrument 100 may be guided to the penetration hole along the tapered surface due to the centering member 53A, the insertion section 102 of the endoscope treatment instrument 100 may follow the center axis line O3 of the operation stick 51.

As shown in FIG. 5, the coil spring 52 is a tensile spring of which one end is fixed to the end of the operation stick 51 and the other end is fixed to a frame 55 to be described later in the first tilting mechanism 54. Accordingly, in a state where no external force is applied to the operation stick 51, the operation stick 51 is supported by the coil spring 52 in a direction in which the center axis line of the coil spring 52 has a linear shape. The position of the operation stick 51 at this time is the neutral position of the operation stick 51.

As shown in FIG. 4, the first tilting mechanism 54 includes the frame 55, a swinging member 56 which is connected to the frame 55 so as to be able to swing, a second pulley 60 which is connected to the frame 55 and is fitted into the swinging member 56, and a clutch mechanism 63 which is provided so as to be able to contact the swinging member 56 and the second pulley 60.

The frame 55 is fixed to the operation section 30 (see FIG. 1A), and supports the swinging member 56, the second pulley 60, and the clutch mechanism 63. The frame 55 includes a pair of plate-like portions 55A and 55B which are provided in parallel. The plate-like portion 55A is provided with a penetration hole 55C which supports the swinging member 56 so as to be rotatable. Further, the plate-like portion 55B is provided with a penetration hole 55D which supports the second pulley 60 so as to be rotatable. The penetration hole 55C and the penetration hole 55D are arranged in a coaxial shape, and the swinging member 56 and the second pulley 60 are supported by the frame 55 so as to be rotatable about the center axis line (the rotation axis O4) of the penetration hole 55C and the penetration hole 55D.

The swinging member 56 rotates about the rotation axis O4 when the operation stick 51 is tilted from the neutral position. The swinging member 56 is provided with a swinging main body 56A which is provided with the penetration hole portion 56B, a connection shaft 56C, a clutch engagement portion 57, a support member 58, and two contact members 59 which are spaced from each other (see FIG. 3).

The shape of the swinging main body 56A is a prismatic cylinder shape in which a penetration hole portion 56B is formed so as to have an axis extending in a direction perpendicular to the rotation axis O4. Further, a protrusion which is fitted to the penetration hole formed in the plate-like portion 55A of the frame 55 is formed in the outer surface of the swinging main body 56A. The operation stick 51 is inserted through the inside of the penetration hole portion 56B which is formed in the swinging main body 56A. The shape of the penetration hole portion 56B is formed so that the cross-sectional shape perpendicular to the axial direction is a rectangular shape. More specifically, the rectangular shape in the penetration hole portion 56B is formed so that the long edge is parallel to the rotation axis O4 and the dimension of the short edge is approximately equal to the diameter of the operation stick 51.

The connection shaft 56C supports the operation stick 51 with respect to the swinging member 56 so as to be rotatable about the rotation axis O5 perpendicular to the rotation axis O4. The connection shaft 56C penetrates the outer wall of the operation stick 51, and crosses the penetration hole portion 56B in the direction of the short edge. The connection shaft 56C is provided with a penetration hole 56D which has an inner diameter for allowing the insertion section 102 of the endoscope treatment instrument 100 to be inserted therethrough, and the insertion section of the endoscope treatment instrument may communicate with the treatment instrument channel 12 from the operation stick 51 through the penetration hole 56D.

The clutch engagement portion 57 is formed in a columnar shape which is formed about the rotation axis O4. The clutch engagement portion 57 is provided with a columnar fitting shaft 57A which is coaxial with the clutch engagement portion 57. The size of the diameter of the fitting shaft 57A is smaller than the size of the diameter of the clutch engagement portion 57.

The support member 58 is formed in a columnar shape which is formed about the center axis line (the rotation axis O6) parallel to the rotation axis O4.

Two contact members 59 are respectively formed in a prismatic shape in the direction parallel to the rotation axis O4. The opposite wall surfaces of the two contact members 59 are formed in parallel to each other.

The second pulley 60 includes a cylindrical clutch engagement portion 61 and a pulley portion 62 which is coaxial with the clutch engagement portion 61.

The clutch engagement portion 61 includes a fitting hole 61A into which the fitting shaft 57A is inserted. Further, the dimension of the outer diameter of the clutch engagement portion 61 is equal to the dimension of the outer diameter of the clutch engagement portion 57. The dimension of the inner diameter of the fitting hole 61A in the clutch engagement portion 61 is slightly larger than the dimension of the outer diameter of the fitting shaft 57A. The second pulley 60 is connected to the clutch engagement portion 57 of the swinging member 56 so as to be rotatable about the rotation axis O4.

As shown in FIGS. 2 to 4, the input wire 85 of the second transmission portion 84 to be described later is wound on the circumference of the pulley portion 62 about the rotation axis O4. The pulley portion 62 engages with the input wire 85 through the friction therebetween. It is desirable that the pulley diameter d2 of the pulley portion 62 be smaller than the pulley diameter d1 of the first pulley 44 in the rotation input portion 40.

The clutch mechanism 63 includes a clutch spring 64 and a releasing mechanism 65.

As shown in FIGS. 3 and 6, the clutch spring 64 is formed in a shape in which the plate material is curved in a substantially cylindrical shape and both end portions 64A and 64B in the circumferential direction is bent outward in the radial direction of the cylinder. Further, the clutch spring 64 is formed of a material having elasticity. Both end portions 64A and 64B of the clutch spring 64 are inserted between two contact members 59 so that a clutch opening member 68 to be described later is interposed between the end portions 64A and 64B.

As shown in FIG. 4, the clutch spring 64 is connected to the clutch engagement portion 57 by a fixing screw 64C. The clutch spring 64 and the clutch engagement portion 57 do not need to be fixed, and may be positioned so that the clutch spring 64 and the clutch engagement portion 57 do not relatively rotate about the rotation axis O4.

The inner diameter of the cylinder of the clutch spring 64 is smaller than the outer diameters of the clutch engagement portions 57 and 61 in a state where no external force is applied thereto. Accordingly, the clutch spring 64 may connect the swinging member 56 and the second pulley 60 to each other in a manner such that the clutch engagement portions 57 and 61 are fastened to each other by the elastic force of the clutch spring 64. When the clutch engagement portions 57 and 61 are fastened to each other by the elastic force of the clutch spring 64, the clutch spring 64 allows the clutch engagement portions 57 and 61 and the clutch spring 64 to engage with each other through the friction therebetween, so that the swinging member 56 and the second pulley 60 are connected such that the swinging member 56 and the second pully can rotate together about the rotation axis O4.

As shown in FIG. 4, the releasing mechanism 65 releases the constriction of the clutch spring 64 with respect to the clutch engagement portion 57 and the clutch engagement portion 61. The releasing mechanism 65 includes the clutch opening member 68 which is inserted through the support member 58 and a releasing member 66 which is fixed to the frame 55.

As shown in FIGS. 6 and 7, the clutch opening member 68 is supported by the support member 58 so as to be rotatable about the rotation axis O6. The shape of the clutch opening member 68 is formed so that the cross-section perpendicular to the rotation axis O6 has an oval shape, and is formed in a cylindrical shape which extends in the rotation axis O6. Further, with regard to the dimension of the clutch opening member 68 in the cross-section perpendicular to the rotation axis O6, the maximal dimension X1 is larger than the distance W1 between both end portions 64A and 64B when the clutch spring 64 fastens the clutch engagement portions 57 and 61 to each other, and the minimal dimension X2 is equal to or smaller than the distance w1.

As shown in FIGS. 4 and 6, when the clutch opening member 68 rotates about the rotation axis O6, both end portions 64A and 64B of the clutch spring 64 are pressed by the outer peripheral surface of the clutch opening member 68, and the distance between both end portions 64A and 64B becomes larger than the distance w1. Then, the clutch spring 64 is elastically deformed, so that the dimension of the inner diameter of the cylinder of the clutch spring 64 becomes larger. Accordingly, the clutch spring 64 is separated from the outer peripheral surfaces of the clutch engagement portion 57 and the clutch engagement portion 61. As a result, the swinging member 56 and the second pulley 60 are relatively rotatable about the rotation axis O4.

As shown in FIGS. 3 and 4, the releasing member 66 is formed in a gate shape which surrounds the clutch spring 64 and the clutch opening member 68 when seen from the direction of the axis O4. The releasing member 66 includes leg portions 66A and 66B which extend from the frame 55 and are parallel to each other and a beam portion 66c which is formed across tip ends of the leg portion 66A and the leg portion 66B. The center portion of the beam portion 66C is provided with a contact protrusion 67 which protrudes toward the rotation axis O4.

As shown in FIGS. 3 and 6, the contact protrusion 67 is formed in a V-shape of which the width becomes narrower as it is closer toward the clutch opening member 68. Further, the protruding end 67A of the contact protrusion 67 is positioned between the beam portion 66C and the support member 58, and when the operation stick 51 is present at the neutral position, the outer surface of the contact protrusion 67 comes into contact with the outer surface of the clutch opening member 68. Accordingly, when the operation stick 51 is tilted from the neutral position, the second driving force is transmitted from the tilt input portion 50 to an input wire 85 to be described later, so that the tilt input portion 50 and the input wire 85 may move in a synchronized manner. When the tilt input portion 50 is present at the neutral position, the synchronization between the tilt input portion 50 and the input wire 85 may be released.

The second tilting mechanism 69 has substantially the same shape as that of the first tilting mechanism 54, but has a difference in that the swinging member 56 and the second pulley 60A rotate about the rotation axis O7 (see FIG. 2) perpendicular to the rotation axis O4 in the first tilting mechanism 54 and the operation stick 51 is not inserted into the swinging member 56 but the extension member 70 engaging with the operation stick 51 is attached thereto. Hereinafter, the same reference signs will be used to the same components as those of the first tilting mechanism 54 and a description thereof will not be repeated here.

The second pulley 60A has the same shape and size as those of the second pulley 60, but has a difference in that an input wire 86 of the second transmission portion 84 to be described later is wound thereon.

The extension member 70 connects the operation stick 51 and the swinging member 56 to each other. The extension member 70 is formed in a frame shape in which one end of the extension member 70 is fixed to the swinging member 56 and the other end thereof is provided with a penetration hole portion 70A used for allowing the operation stick 51 to be inserted therethrough.

The penetration hole portion 70A is provided with a pair of wall portions 71. When the operation stick 51 is tilted about the rotation axis O7, the pair of wall portions 71 comes into contact with the operation stick 51. The distance between the pair of wall portions 71 is substantially equal to the diameter of the operation stick 51.

In the embodiment, the tilt input portion 50 may tilt the operation stick 51 from the neutral position within a predetermined constant movable range.

Further, as shown in FIGS. 1 and 2, the operation mechanism 32 includes the first transmission portion (the first transmission means) 20 which is connected to the rotation input portion 40 and the curved portion 13 and the second transmission portion (the second transmission means) 84 which is connected to the rotation input portion 40 and the tilt input portion 50.

The first transmission portion 20 transmits the first driving force which is input to the rotation input portion 40 to the curved portion 13. The first transmission portion 20 includes the driving wire 24 which is hung on the disk member 43, two operation wires 22, both ends of which are respectively fixed to both ends of the driving wire 24 and the curved portion 13, the driving wire 25 which is hung on the disk member 47, and two operation wires 23 the ends of which are respectively fixed to both ends of the driving wire 25.

The operation wires 22 and 23 are, for example, linear flexible wires formed in a stranded wire shape which are respectively fixed to the distal end 13A of the curved portion 13. As the materials of the operation wires 22 and 23, for example, stainless steel may be adopted. The operation wires 22 and 23 are pulled through the driving wires 24 and 25 in a manner such that the disk members 43 and 47 of the rotation input portion 40 are rotated, thereby transmitting the first driving force to the curved portion 13. The curved portion 13 may be curved in the curving direction corresponding to the pulled operation wire using the operation wires 22 and 23.

As shown in FIG. 2, the second transmission portion 84 is connected to the tilt input portion 50 and the rotation input portion 40, and transmits the second driving force from the tilt input portion 50 to the rotation input portion 40. The second transmission portion 84 includes input wires 85 and 86 which are connected by being wound on the first pulleys 44 and 48 of the rotation input portion 40.

The input wires 85 and 86 transmit the second driving force which is input to the tilt input portion 50 to the rotation input portion 40. The input wires 85 and 86 are, for example, linear flexible wires formed in a stranded wire shape. As the materials of the input wires 85 and 86, for example, stainless steel may be adopted. The input wire 85 is wound on the second pulley 60 of the first tilting mechanism 54. Further, the input wire 86 is wound on the second pulley 60A of the second tilting mechanism 69.

Since the disk member 43 and the first pulley 44 are fixed to each other and the disk member 47 and the first pulley 48 are fixed to each other, the second driving force which is transmitted from the tilt input portion 50 by the input wires 85 and 86 of the second transmission portion 84 is transmitted to the curved portion 13 by the first transmission portion 20. That is, at this time, the first transmission portion 20 moves in the direction of the center axis line of the insertion section 10 due to the second driving force. That is, the curved portion 13 may be curved by any one of the first driving force and the second driving force.

Further, the second transmission portion 84 is provided with an angle roller portion 87 which directs the directions of the input wires 85 and 86 toward the first pulleys 44 and 48.

The angle roller portion 87 includes angle rollers 88 and 89 provided with a cylindrical surface shaped outer peripheral surface. The input wire 85 is hung on the outer peripheral surface of the angle roller 88, and the input wire 86 is hung on the outer peripheral surface of the angle roller 89. In the embodiment, the angle rollers 88 and 89 are respectively formed in a columnar shape.

The operation of the endoscope apparatus 1 of the embodiment with the above-described configuration in use will be described.

When the endoscope apparatus 1 is used, first, the insertion section 10 of the endoscope apparatus 1 is manually inserted from the distal end 10A into the body cavity by the operator. Then, the image inside the body cavity is captured by using the observation means 14 (see FIG. 1) which is installed in the distal end 10A of the insertion section 10, and the treatment subject portion is observed through the use of the image which is captured by the observation means 14 and is displayed on an external display device (not shown). At this time, the operator curves the curved portion 13 using the first angle knob 42 and the second angle knob 46 of the rotation input portion 40, and may direct the distal end 10A of the insertion section 10 toward the treatment subject portion.

As shown in FIGS. 2 and 8, when the observation of the treatment subject portion is ended, the operator inserts the insertion section 102 of the endoscope treatment instrument 100 into the operation stick 51 of the tilt input portion 50 from its treatment portion 101. At this time, the insertion section 102 of the endoscope treatment instrument 100 advances into the penetration hole 56D of the connection shaft 56C along the center axis line O3 of the operation stick 51 by the centering member 53A which is provided inside the operation stick 51, so that it is inserted into the treatment instrument channel 12. The operator allows the treatment portion 101 to protrude from the distal end 10A of the insertion section 10 through the inside of the treatment instrument channel 12. Further, a part of the operation section 103 of the endoscope treatment instrument 100 is inserted into the operation stick 51.

When the endoscope treatment instrument 100 is attached to the endoscope apparatus 1, the operator grips the grip portion 31 of the endoscope apparatus 1 by one hand and grips the grip portion 104 of the endoscope treatment instrument 100 by the other hand. In this state, the operator tilts the operation stick 51 from the neutral position while gripping the grip portion 104. Then, the first tilting mechanism 54 and the second tilting mechanism 69 swing in a direction in which the operation stick 51 is tilted.

For example, the first tilting mechanism 54 swings about the rotation axis O4 when the operation stick 51 is tilted. Then, as shown in FIGS. 3 and 7, the clutch spring 64 of the clutch mechanism 63 connects the swinging member 56 to the second pulley 60 by fastening the clutch engagement portions 57 and 61 to each other. Accordingly, the second driving force which is input from the operator through the operation stick 51 may be transmitted from the swinging member 56 to the second pulley 60. If the operator tilts the operation stick 51 when the clutch spring 64 connects the swinging member 56 to the second pulley 60, a force in which the operator tilts the operation stick 51 is converted into a force which rotates the second pulley 60 through the clutch spring 64 of the clutch mechanism 63. Accordingly, the second pulley 60 rotates about the rotation axis O4. When the second pulley 60 rotates about the rotation axis O4, a force which rotates the second pulley 60 is converted into a force which pulls the input wire 85. Then, the input wire 85 is pulled by the second pulley 60. When the input wire 85 is pulled, the first pulley 44 on which the input wire 85 is hung and wound rotates about the rotation axis O2.

Here, since the pulley diameter d2 of the pulley portion 62 is smaller than the pulley diameter of the first pulley 44 in the rotation input portion 40, when the pulley portion 62 rotates about the rotation axis O4 by a predetermined angle, the first pulley 44 rotates by an angle which is smaller than the above-described predetermined angle in which the second pulley 60 rotates. Further, when the first pulley 44 rotates, the disk member 43 which is fixed to the first pulley 44 also rotates about the rotation axis O2. Accordingly, the driving wire 24 which is hung and wound on the disk member 43 moves so as to pull the operation wire 22. When the operation wire 22 is pulled, the curved portion 13 is curved in the curving direction corresponding to the pulled operation wire.

In the same way, when the operation stick 51 is tilted about the rotation axis O7, the operation wire 23 is pulled, and the curved portion 13 is curved in the curving direction corresponding to the pulled operation wire.

At this time, the length in which the operation wires 22 and 23 are pulled when the operation stick 51 is tilted by a predetermined angle is smaller than the length in which the operation wires 22 and 23 are pulled when the first angle knob 42 and the second angle knob 46 of the rotation input portion 40 are rotated by the above-described predetermined angle.

As a result, when the curved portion 13 is curved by using the operation stick 51, the curved angle becomes smaller than the angle when the curved portion 13 is curved by using the first angle knob 42 and the second angle knob 46, and the treatment portion 101 of the endoscope treatment instrument 100 may be slightly moved relative to the treatment subject portion.

When the operator detaches the hand from the operation stick 51 or loosens the hanging force on the operation stick 51, the operation stick 51 returns to the original neutral position due to the coil spring 52 which is fixed to the operation stick 51. At this time, the curved state of the curved portion 13 changes as much as an extent in which the operation stick 51 returns to the neutral position. When the operation stick 51 returns to the neutral position, the clutch opening member 68 comes into contact with the contact protrusion 67 and rotates about the rotation axis O6. Then, the distance between both end portions 64A and 64B of the clutch spring 64 is widened by an extent larger than the distance w1, so that the connection between the clutch engagement portion 57 and the clutch engagement portion 61 is released (see FIG. 6). Accordingly, the swinging member 56 and the second pulley 60 are rotatable about the rotation axis O4 again.

When the second driving force input from the operator by using the operation stick 51 is transmitted to the second tilting mechanism 69, the force which tilts the operation stick 51 is converted into a force which rotates the swinging member 65 of the second tilting mechanism 69 about the rotation axis O7 (see FIG. 2) through the extension member 70. Accordingly, the second pulley 60A is rotated by the same action as that of the first tilting mechanism 54, and the first pulley 48 rotates about the rotation axis O2 through the input wire 86 which is hung and wound on the second pulley 60A. As a result, the disk member 47 rotates about the rotation axis O2 by the first pulley 48, and the curved portion 13 is curved by the operation wire 23 through the driving wire 25.

When the operator moves the operation section 103 of the endoscope treatment instrument 100 forward and backward in the direction of the center axis of the operation stick 51 (the directions Z1 and Z2 shown in FIG. 8), the amount in which the endoscope treatment instrument 100 protrudes from the distal end 10A of the insertion section 10 of the endoscope apparatus 1 changes. Further, when the operation section 103 of the endoscope treatment instrument 100 is rotated about the center axis of the operation stick 51 (the directions Y1 and Y2 shown in FIG. 8), the treatment portion 101 of the endoscope treatment instrument 100 rotates about the axis of the insertion section 102 of the endoscope treatment instrument 100.

In this way, the curved portion 13 of the endoscope apparatus 1 may be made to be curved and the endoscope treatment instrument 100 may be made to protrude and rotate by using the tilt input portion 50 and the endoscope treatment instrument 100 attached to the tilt input portion 50.

Conventionally, in a case where a treatment is performed on a tissue of a living body using the endoscope apparatus, the endoscope apparatus and the endoscope treatment instrument may be used simultaneously while the endoscope apparatus is gripped by one hand and the endoscope treatment instrument is gripped by the other hand. At this time, the curved portion of the endoscope apparatus may be curved in order to move the treatment portion of the endoscope treatment instrument with respect to the treatment subject portion. However, in the existing endoscope apparatus, the curving operations in two axial directions perpendicular to each other are input by rotating two angle knobs, but it is difficult to recognize the rotating direction of the angle knob and the curving direction of the curved portion.

On the contrary, according to the endoscope apparatus 1 that includes the operation mechanism 32 of the embodiment, since the endoscope apparatus 1 includes the tilt input portion 50 in addition to the rotation input portion 40, it is possible to intuitively operate the curved portion 13 using the tilt input portion 50 compared to the rotation in the rotation input portion 40.

Further, the rotation input portion 40 may freely rotate about the rotation axis O2, the tilt input portion 50 may tilt the operation stick 51 within a predetermined movable range, and the tilt input portion 50 includes the clutch mechanism 63. Accordingly, even when the rotation input portion 40 rotates about the rotation axis O2, if the operation stick 51 is present at the neutral position, the operation stick 51 is not operated. As a result, it is possible to suppress the useless operation of the operation stick 51 and the operation stick 51 can operate the rotation input portion 40 regardless of the movable range of the operation stick 51.

Further, since the length in which the operation wires 22 and 23 are pulled when the operation stick 51 is tilted by a predetermined angle is shorter than the length in which the operation wires 22 and 23 are pulled when the rotation input portion is rotated by a predetermined angle, a delicate curving operation of the curved portion 13 may be highly precisely performed by using the operation stick 51. Further, when the endoscope treatment instrument 100 is used while being attached to the operation stick 51, the treatment portion 101 of the endoscope treatment instrument 100 may be slightly moved with respect to the treatment subject portion. However, in this case, the treatment portion 101 may be moved relative to the treatment subject portion with high precision.

Further, since the coil spring 52 which biases the operation stick 51 toward the neutral position is provided, the operation stick 51 may be positioned at the neutral position with a simple configuration.

Further, since the operation stick 51 is formed in a cylindrical shape so as to communicate with the inside of the treatment instrument channel 12, the operation stick 51 may be tilted while the operation section 103 of the endoscope treatment instrument 100 is inserted into the operation stick 51 and the operation section 103 or the grip portion 104 is gripped. As a result, the operation of the endoscope treatment instrument 100 and the operation of the endoscope apparatus 1 may be performed by the hand opposite to the hand which grips the grip portion 31 of the endoscope apparatus 1, and the operation of the treatment instrument operation section, which is performed by an assistant conventionally, may be performed by the operator which operates the endoscope apparatus 1.

While the preferred embodiment of the invention has been described, the invention is not limited to the embodiment. Additions, omissions, substitutions, and other modifications of the configuration may be made without departing from the spirit of the invention.

For example, the operation mechanism 32 which is described in the above-described embodiment may be appropriately applied to the medical device which does not include the observation means 14. For example, the same configuration as that of the operation mechanism 32 of the embodiment may be applied to a guide catheter which is formed in an elongated cylindrical shape, has a lumen allowing a medical device to be inserted therethrough, and has a curved portion formed in its distal end of an insertion direction in which the guide catherter is inserted into a body cavity.

Further, the disk members 43 and 47 may be a sprocket wheel. In this case, it is desirable that the driving wires 24 and 25 are formed in a chain shape which meshes with the sprocket wheel. When the disk members 43 and 47 are the sprocket wheels, it is possible to suppress sliding between the disk members 43 and 47 and the driving wires 24 and 25. As a result, the curved portion 13 may be highly precisely curved by reliably pulling the operation wires 22 and 23 through the driving wires 24 and 25.

Further, the operation mechanism 32 which is described in the above-described embodiment is not limited to the combination of the input of the driving force generated by the rotating operation and the input of the driving force generated by the tilting operation. For example, when two input means are simultaneously provided so that at least any one of them has a restricted movable range, the operation mechanism described in the embodiment may be appropriately applied.

In addition, the invention is not limited to the above-described embodiment, and is limited only to the appended claims.

An operation mechanism and a medical device of a second embodiment of the invention will be described. In the description below, as an example of the medical device of the embodiment, an endoscope apparatus 105 will be described by referring to the drawings, where a human body or the like is set as a subject, and the inside of the alimentary canal of the subject or the tissue inside the living body is observed and treated.

Figure 9:
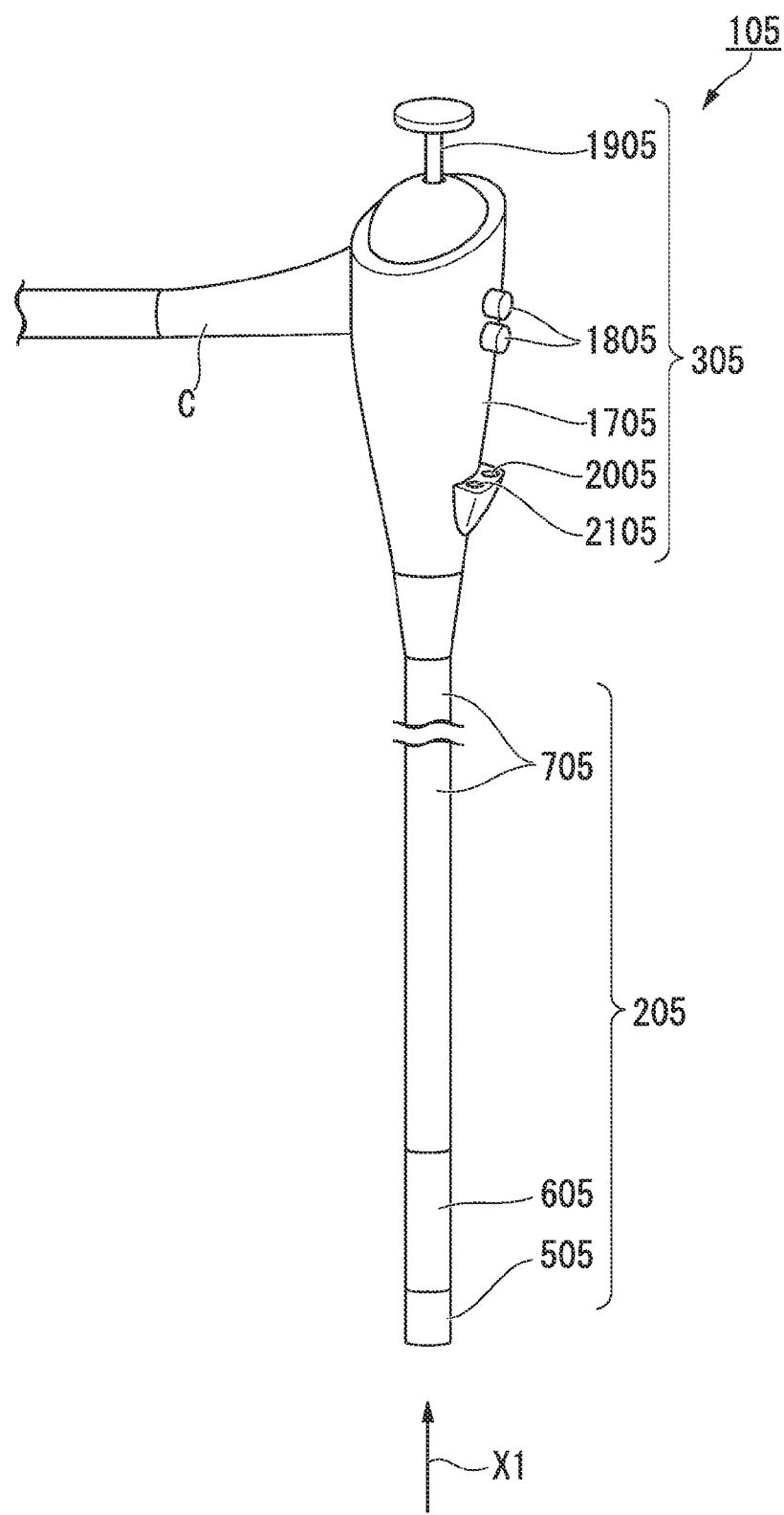
FIG. 9 is a front view illustrating an endoscope apparatus according to an embodiment of the invention.
Figure 10:
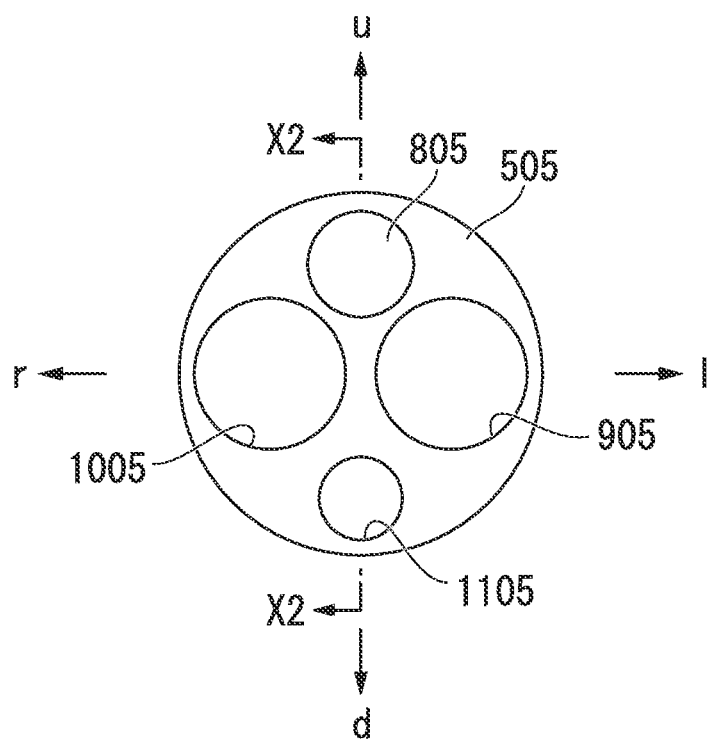
FIG. 10 is a diagram when seen from X1 of FIG. 1.
Figure 11:
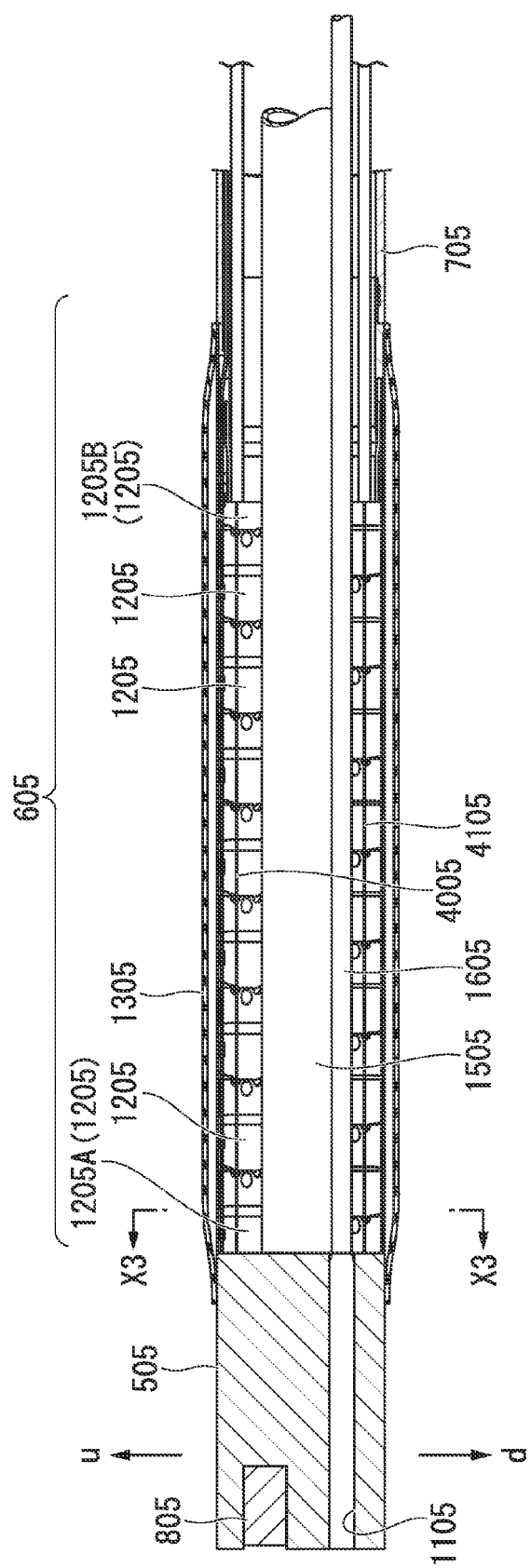
FIG. 11 is a cross-sectional view taken along the line X2-X2 of FIG. 2.
Figure 12:
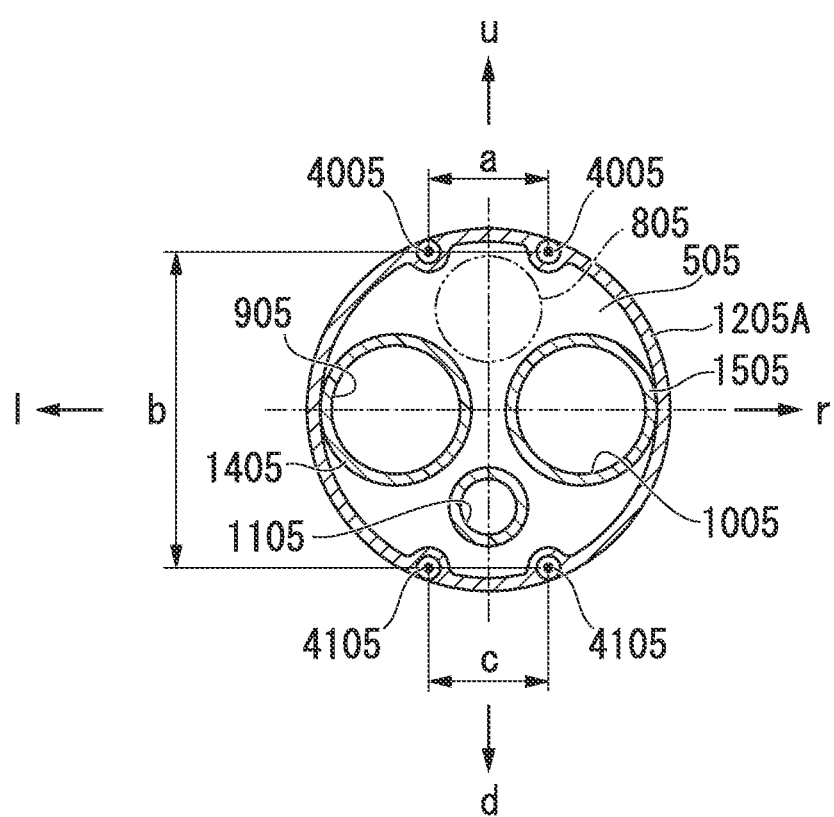
FIG. 12 is a cross-sectional view taken along the line X3-X3 of FIG. 3.
Figure 13:
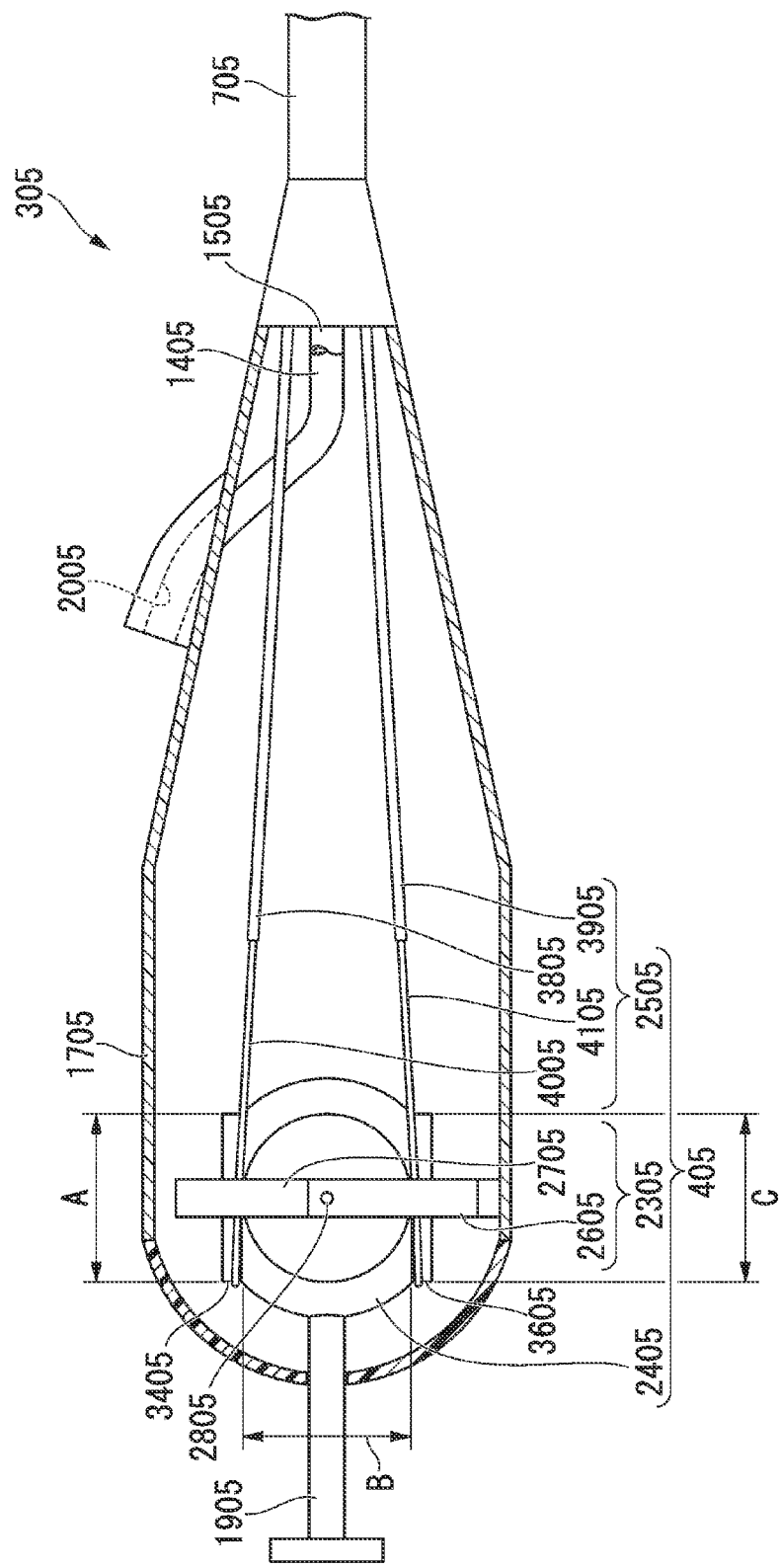
FIG. 13 is a partial cross-sectional view illustrating the internal configuration of an operation section in the endoscope apparatus.
Figure 14:
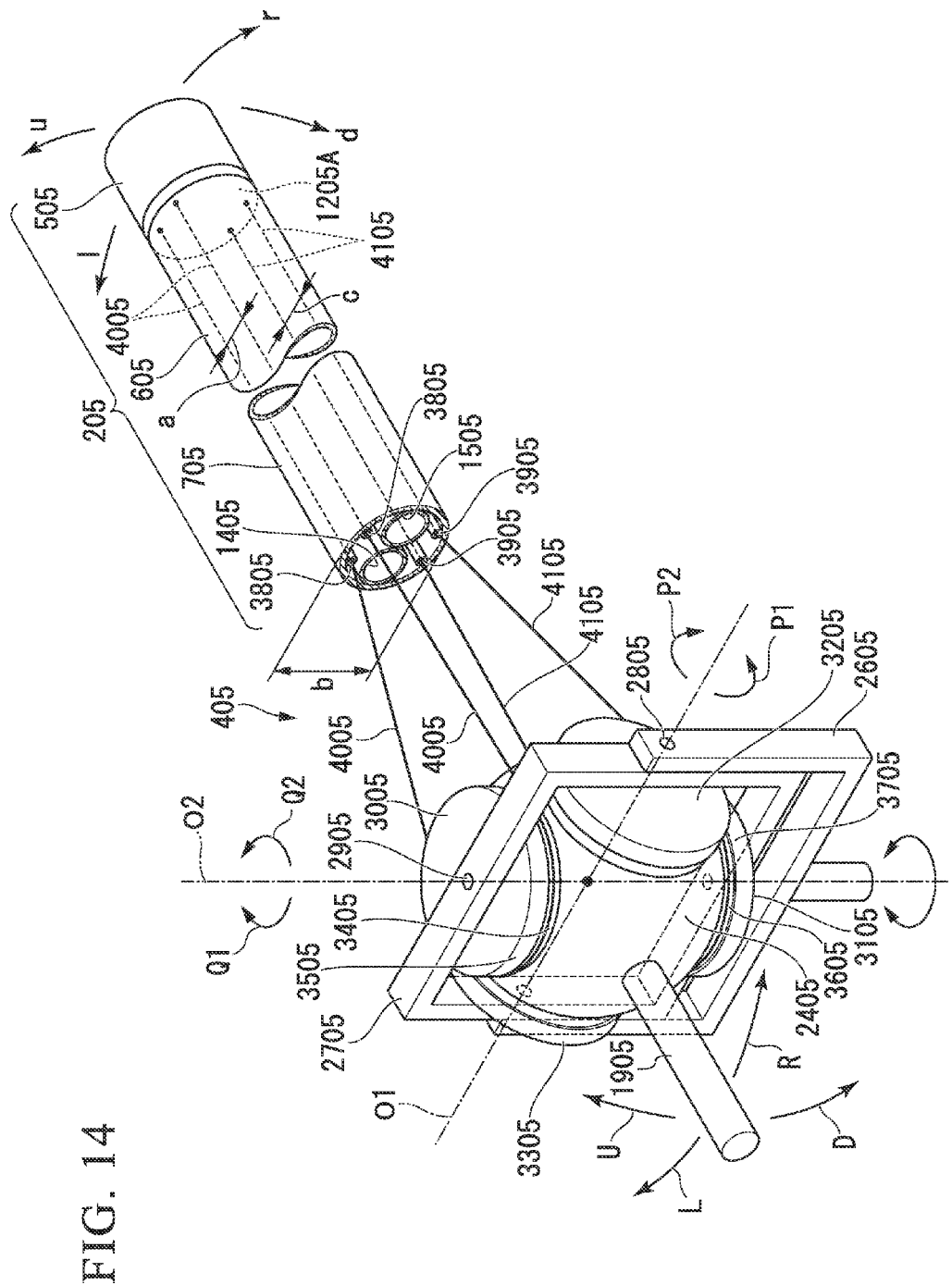
FIG. 14 is a perspective view illustrating the configuration of an operation mechanism in the endoscope apparatus.

FIG. 9 is a front view illustrating an endoscope apparatus 105. Further, FIG. 10 is a diagram when seen from X1 of FIG. 9. Further, FIG. 11 is a cross-sectional view taken along the line X2-X2 of FIG. 10. Further, FIG. 12 is a cross-sectional view taken along the line X3-X3 of FIG. 11. Further, FIG. 13 is a partial cross-sectional view illustrating the internal configuration of an operation section 305 in the endoscope apparatus 105. Further, FIG. 14 is a perspective view illustrating the configuration of an operation mechanism 405 in the endoscope apparatus 105.

As shown in FIG. 9, the endoscope apparatus 105 includes an insertion section 205 which is inserted into an alimentary canal or a body cavity of the subject, an operation section 305 which is connected to the proximal end of the insertion section 205 and is used to operate the insertion section 205, and an operation mechanism 405 (see FIG. 13) which is provided inside the operation section 305.

The insertion section 205 includes a distal end component portion 505 which is provided in the distal end of the insertion section 205, a curved portion 605 which is connected to the proximal end of the distal end component portion 505, and a flexible portion 705 which is formed in a flexible tube shape and connected to the proximal end of the curved portion 605 and the distal end of the operation section 305.

As shown in FIG. 10, the distal end component portion 505 includes an imaging portion 805 which has, for example, an image sensor and captures an image in front of the distal end component portion 505, a first protruding opening portion 905 and a second protruding opening portion 1005 which allow a treatment instrument used for performing a treatment on a tissue of a living body protrude from its distal end, and a port 1105 which is opened so as to perform an air/water feeding operation or a suctioning operation.

For convenience of the description, hereinafter, the description will be made by setting the upside, the downside, the left side, and the right side so that the imaging portion 805 side of the distal component portion 505 is set as the upside u, the port 1105 side of the distal component portion 505 is set as the downside d, the first protruding opening portion 905 side of the distal component portion 505 is set as the left side 1, and the second protruding opening portion 1005 side of the distal component portion 505 is set as the right side r. These marks correspond to the upside, the downside, the left side, and the right side when the insertion section 205 is seen from the proximal end toward the distal end (see FIG. 12). Furthermore, the arrangement of the imaging portion 805 and the port 1105 is not limited thereto.

As shown in FIG. 11, the curved portion 605 includes plural node ring members 1205 which are arranged from the proximal end toward the distal end and a flexible tubular coating member 1305 which covers the outer peripheries of the plural node ring members 1205, and is formed in a cylindrical shape. In the plural node ring members 1205, a distal end node ring member 1205A which is disposed closest to the distal end is fixed to the proximal end of the distal end component portion 505. In the plural node ring members 1205, a proximal end node ring member 1205B which is disposed closest to the proximal end is fixed to the distal end of the flexible portion 705.

In the plural node ring members 1205, the other node ring members 1205 except for the distal end node ring member 1205A and the proximal end node ring member 1205B respectively include a rotation axis portion, in which the rotation axis line is present within a plane parallel to the radial cross-section of the curved portion 605, at each of the distal end and the proximal end, and they are rotatably connected to each other. In each of the plural node ring members 1205, the rotation axis line which is positioned at the distal end is perpendicular to the rotation axis line positioned at the proximal end.

In the embodiment, the rotation axis lines, which are perpendicular to each other in the node ring members 1205, respectively extend the up-down direction (in FIG. 12, the sides indicated by the reference signs u and d) and the left-right direction (in FIG. 12, the sides indicated by the reference signs 1 and r) of the curved portion 605. When the plural node ring members 1205 rotate about the rotation axis lines, the curved portion 605 may be freely curved in the up-down direction and the left-right direction. Furthermore, when the curving operations of the curved portion 605 in the up-down direction and the left-right direction are synthesized with each other, the curved portion 605 may be freely curved in an arbitrary direction.

As shown in FIGS. 11 and 12, the inside of the curved portion 605 is provided with first channel sheaths 1405 and second channel sheaths 1505, a tube 1605 which communicates with the inside of the port 1105, and a first angle wire 4005 and a second angle wire 4105 to be described later.

The first channel sheaths 1405 and the second channel sheaths 1505 are respectively formed as flexible cylindrical members. As shown in FIG. 12, the first channel sheaths 1405 and the second channel sheaths 1505 are arranged at the left and right inside the curved portion 605, and extend inside the operation section 305 through the inside of the flexible portion 705. In the first channel sheaths 1405 and the second channel sheaths 1505, the respective distal ends are fixed to the proximal ends of the first protruding opening portion 905 and the second protruding opening portion 1005 of the distal end component portion 505. In the first channel sheaths 1405 and the second channel sheaths 1505, the respective proximal ends are connected to insertion opening portions 2005 and 2105 which are provided in the operation section 305 (see FIG. 9).

As shown in FIG. 9, the operation section 305 includes an outer wall member 1705 which has an external shape formed as a substantially columnar shape and has a hollow structure. The outer surface of the operation section 305 is provided with an air-water feeding switch 1805 which performs an air/water feeding operation or a suctioning operation from the port 1105 of the distal end component portion 505, a substantially bar-like tilt input portion 1905 which protrudes from the proximal end of the operation section 305 so as to input an operation for curving the curved portion 605, and a first insertion opening portion 2005 and a second insertion opening portion 2105 which penetrate the outer wall member 1705 of the operation section 305 so as to insert the treatment instrument into the first channel sheaths 1405 and the second channel sheaths 1505.

In the embodiment, the positional relationship between the air-water feeding switch 1805 and the tilt input portion 1905 are set as a positional relationship in which fingers may reach both the air-water feeding switch 1805 and the tilt input portion 1905 when the operator who operates the endoscope apparatus 105 grips the outer surface of the operation section 305.

Further, the proximal end of the outer wall member 1705 of the operation section 305 is formed of, for example, rubber or the like so as to have flexibility.

The proximal end of the tilt input portion 1905 is made so that fingers of the operator of the endoscope apparatus 105 can touch so as to tilt the tilt input portion 1905, and is formed in a flange shape which extends outward in the radial direction.

Further, a universal cable C may be connected to the operation section 305 so that power is supplied to the imaging portion 805 or an image captured inside the imaging portion 805 is transmitted to the outside.

As shown in FIG. 13, the inside of the operation section 305 communicates with the inside of the flexible portion 705, and the first channel sheaths 1405 and the second channel sheaths 1505 which extend from the flexible portion 705 are pulled into the operation section 305. The proximal ends of the first channel sheaths 1405 are connected to the distal end of the first insertion opening portion 2005. Although not shown in the drawings, the proximal end of the second channel sheath 1505 is connected to the distal end of the second insertion opening portion 2105. Accordingly, each of the lumen from the first insertion opening portion 2005 to the first protruding opening portion 905 and the lumen from the second insertion opening portion 2105 to the second protruding opening portion 1005 is formed as a pipe line through which a treatment instrument or the like performing a treatment on a tissue of a living body is carried out to the distal end of the insertion section 205.

The inside of the operation section 305 is provided with the operation mechanism 405 to which the distal end of the tilt input portion 1905 is fixed. The operation mechanism 405 includes a movable support portion 2305 which is fixed to the outer wall member 1705 of the operation section 305, a swinging member 2405 which is supported by the movable support portion 2305, and a transmission portion 2505 which is connected to the swinging member 2405.

As shown in FIGS. 13 and 14, the movable support portion 2305 includes a first support body 2605 and a second support body 2705.

The first support body 2605 extends inward from the inner surface of the outer wall member 1705 of the operation section 305 so that one end of the first support body 2605 is fixed to the outer wall member 1705 of the operation section 305 and the other end thereof is formed in a fork shape. The other ends of the first support body 2605 are respectively provided with two first swing connection portions 2805 which connect the second support body 2705 in a swingable manner. The first tilt axis O1 about which the second support body 2705 swings relative to the first support body 2605 is defined by the two first swing connection portions 2805.

The second support body 2705 is formed in a frame shape which surrounds the swinging member 2405, and is connected to the first swing connection portion 2805 of the first support body 2605. Accordingly, the second support body 2705 is configured to be rotatable about the first tilt axis O1 relative to the first support body 2605. Further, the second support body 2705 is provided with two second swing connection portions 2905 which connect the swinging member 2405 in a swingable manner. The second tilt axis O2 about which the swinging member 2405 swings relative to the second support body 2705 is defined by the two second swing connection portions 2905. The second tilt axis O2 is perpendicular to the first tilt axis O1. The swinging member 2405 is connected to the second support body 2705 so as to be swingable about the second tilt axis O2. The swinging member 2405 is formed in a substantially spherical shape in which the intersection between the first tilt axis O1 and the second tilt axis O2 becomes a sphere center. The swinging member 2405 is provided with a first pulley portion 3005 and a second pulley portion 3105 which face each other with the sphere center of the swinging member 2405 interposed therebetween and have a cylindrical surface formed about the second tilt axis O2, and a first wire guide 3205 and a second wire guide 3305 which face each other with the sphere center of the swinging member 2405 interposed therebetween and have a cylindrical surface formed about the first tilt axis O1.

Hereinafter, for convenience of description, as shown in FIG. 14, the tilting direction of the tilt input portion 1905 is marked so that the direction from the sphere center of the swinging member 2405 toward the first pulley portion 3005 is set as the up direction U, the direction from the sphere center of the swinging member 2405 toward the second pulley portion 3105 is set as the down direction D, the direction from the sphere center of the swinging member 2405 toward the first wire guide 3205 is set as the right direction R, and the direction from the sphere center of the swinging member 2405 toward the second wire guide 3305 is set as the left direction L.

The first pulley portion 3005 is formed in a disk shape, and includes a first circular arc portion 3405 which is provided with a cylindrical surface shaped outer peripheral surface formed about the second tilt axis O2 and a first retaining portion 3505 which has a diameter larger than the outer diameter of the first circular arc portion 3405. The first circular arc portion 3405 is positioned at the sphere center of the swinging member 2405 side of the first retaining portion 3505.

Further, the second pulley portion 3105 is formed in the same disk shape as that of the first pulley portion 3005, and includes a second circular arc portion 3605 which is provided with a cylindrical surface shaped outer peripheral surface formed about the second tilt axis O2 and a second retaining portion 3705 which has a diameter larger than the outer diameter of the second circular arc portion 3605. The second circular arc portion 3605 is positioned at the sphere center of the swinging member 2405 side of the second retaining portion 3705. As shown in FIG. 13, in the embodiment, the diameter A of the first circular arc portion 3405 is equal to the diameter C of the second circular arc portion 3605.

Each of the first wire guide 3205 and the second wire guide 3305 has a cylindrical surface whose diameter is the same as the diameter A of the first circular arc portion 3405 at a position near the first circular arc portion 3405, and has a cylindrical surface whose diameter is the same as the diameter of the second circular arc portion 3605 at a position near the second circular arc portion 3605. In the embodiment, the respective diameters of the first circular arc portion 3405 and the second circular arc portion 3605 are equal to each other, and the first wire guide 3205 and the second wire guide 3305 are formed in a disk shape which has a cylindrical surface with a center coaxial with the first tilt axis O1.

As shown in FIGS. 13 and 14, the transmission portion 2505 includes two first guide coils 3805 and two second guide coils 3905 which are respectively provided inside the operation section 305 and the flexible portion 705 so as to extend from the operation section 305 to the proximal end of the curved portion 605, a first angle wire 4005 which is inserted through each of the two first guide coils 3805, and a second angle wire 4105 which is inserted through each of the two second guide coils 3905.

The first guide coils 3805 and the second guide coils 3905 are formed of a wire wound in a coil shape, and have flexibility. In the embodiment, the first guide coils 3805 and the second guide coils 3905 are arranged along the inner wall of the flexible portion 705. In the embodiment, the first guide coils 3805 and the second guide coils 3905 are formed of stainless steel. The arrangement of the first guide coils 3805 and the second guide coils 3905 inside the flexible portion 705 will be described below together with the description of the arrangement of the first angle wire 4005 and the second angle wire 4105.

The first angle wire 4005 and the second angle wire 4105 are formed of a wire having flexibility. In the embodiment, the first angle wire 4005 and the second angle wire 4105 are formed of stainless steel.

The intermediate portions of the first angle wire 4005 and the second angle wire 4105 are respectively hung on the first circular arc portion 3405 and the second circular arc portion 3605, and both ends of each of the first angle wire 4005 and the second angle wire 4105 are respectively inserted through the first guide coil 3805 and the second guide coil 3905 so as to extend to the distal end of the curved portion 605.

Further, as shown in FIGS. 11 and 12, both ends of each of the first angle wire 4005 and the second angle wire 4105 are fixed to the distal end node ring member 1205A. Specifically, in the node ring member 1205, the first angle wire 4005 is disposed at the left and right with a distance a therebetween at the upside of the first channel sheaths 1405 and the second channel sheaths 1505 (the u side shown in FIGS. 11 and 12), and the second angle wire 4105 is disposed at the left and right with a distance c at the downside of the first channel sheaths 1405 and the second channel sheaths 1505 (the side d shown in FIGS. 11 and 12). In the embodiment, the distance a and the distance c are equal to each other. Furthermore, the first angle wire 4005 and the second angle wire 4105 are arranged so as to be away from each other by a distance b in the up and down direction. In the embodiment, the distance b is set to be longer than the distance a and the distance c.

As shown in FIG. 14, in the inside of the curved portion 605 and the flexible portion 705, the first angle wire 4005 and the second angle wire 4105 which are inserted through the first guide coil 3805 and the second guide coil 3905 extend in parallel while being respectively away from each other by the distance a and the distance c. Furthermore, the first angle wire 4005 and the second angle wire 4105 extend in parallel while being away from each other by the distance b. In this way, in the inside of the curved portion 605 and the flexible portion 705, the first angle wire 4005 and the second angle wire 4105 are arranged at the positions where they do not interfere with the first channel sheaths 1405 and the second channel sheaths 1505 arranged at the left and the right.

With such a positional relationship, the inner diameters of the first channel sheaths 1405 and the second channel sheaths 1505 may be made larger without changing the outer diameter of the insertion section 205 or the diameter of the insertion section 205 may be made to be smaller without changing the inner diameters of the first channel sheath 1405 and the second channel sheath 1505.

Next, the relationship between the shape and the arrangement position of each of the first circular arc portion 3405 and the second circular arc portion 3605 and the arrangement positions of the first angle wire 4005 and the second angle wire 4105 inside the insertion section 205 will be described in detail.

In the operation mechanism 405 with the above-described configuration, the ratio between the diameter A of the first circular arc portion 3405, the diameter C of the second circular arc portion 3605, and the distance B between the first circular arc portion 3405 and the second circular arc portion 3605 are determined based on the distances a and b between the first angle wires 4005 and the second angle wires 4105 in the node ring member 1205 of the distal end of the curved portion 605 and the distance b between the first angle wire 4005 and the second angle wire 4105.

That is, in the embodiment, the relationship of the diameter A, the diameter C, and the distance B with respect to the distance a, the distance c, and the distance b are set so that distance a:distance b=distance A:diameter B and distance a:distance c=diameter A:diameter C. When this relationship is satisfied, the distance a and the distance c may be different from each other.

Figure 15:
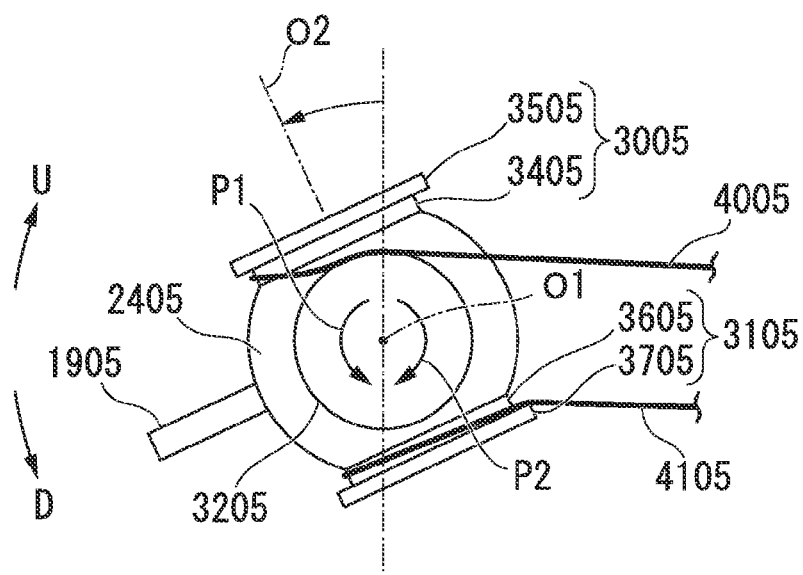
FIG. 15 is an operational diagram illustrating the operation of the operation mechanism in the endoscope apparatus.

The effect of the endoscope apparatus 1 with the above-described configuration will be described. FIG. 15 is an operational diagram illustrating the operation of the operation mechanism 405 in the endoscope apparatus 105.

In a case where the curved portion 605 of the endoscope apparatus 105 is curved, as shown in FIG. 15, the tilt input portion 1905 is tilted by applying a force to the proximal end of the tilt input portion 1905. For example, when the tilt input portion 1905 is tilted in the down direction D, the proximal end of the tilt input portion 1905 is present at the downside relative to the distal end, and the distal end of the tilt input portion 1905 is present at the upside relative to the proximal end.

When the tilt input portion 1905 is tilted, the swinging member 2405 which is fixed to the distal end of the tilt input portion 1905 swings about each of the first tilt axis O1 and the second tilt axis O2.

When the tilt input portion 1905 is tilted in the down direction D, the swinging member 2405 rotates in the counter-clockwise direction (the direction P1 shown in FIG. 15) about the first tilt axis O1 serving as the rotation center when the first tilt axis O1 is seen from the first wire guide 3205 toward the second wire guide 3305. Accordingly, the first circular arc portion 3405 and the second circular arc portion 3605 move in the direction P1 about the first tilt axis O1 serving as the rotation center. Then, the first angle wire 4005 which is hung on the first circular arc portion 3405 is pulled by the first circular arc portion 3405 toward the proximal end, and the second angle wire 4105 which is hung on the second circular arc portion 3605 is loosened. Further, when the first angle wire 4005 is pulled, the first angle wire 4005 comes into contact with the outer peripheral surfaces of the first wire guide 3205 and the second wire guide 3305 so as to be supported by the first wire guide 3205 and the second wire guide 3305.

At this time, as shown in FIG. 14, in the curved portion 605, the distal end node ring member 1205A is pulled toward the proximal end by the first angle wire 4005 which is fixed to the upside of the distal end node ring member 1205A, so that the curved portion 605 is curved in the up direction (in FIG. 14, the side indicated by the reference sign u). Further, when the curved portion 605 is curved in the up direction, the lower second angle wire 4105 is pulled toward the distal end, and the second angle wire 4105 is maintained so as to be hung on the second circular arc portion 3605.

On the contrary, when the tilt input portion 1905 is tilted in the up direction U, the swinging member 2405 rotates in the direction (the direction P2 shown in FIG. 15) opposite to the direction P1. Accordingly, the first circular arc portion 3405 and the second circular arc portion 3605 move in the direction P2 about the first tilt axis O1. Then, the first angle wire 4005 which is hung on the first circular arc portion 3405 is loosened, and the second angle wire 4105 which is hung on the second circular arc portion 3605 is pulled by the second circular arc portion 3605 toward the proximal end. Further, when the second angle wire 4105 is pulled, the second angle wire 4105 comes into contact with the outer peripheral surfaces of the first wire guide 3205 and the second wire guide 3305 so as to be supported by the first wire guide 3205 and the second wire guide 3305.

At this time, as shown in FIG. 14, in the curved portion 605, the distal end node ring member 1205A is pulled toward the proximal end by the second angle wire 4105 which is fixed to the downside of the distal end node ring member 1205A in the manner opposite to the case where the tilt input portion 1905 is tilted in the down direction, so that the curved portion 605 is curved in the down direction (in FIG. 14, the side indicated by the reference sign d). Further, when the curved portion 605 is curved in the down direction, the upper first angle wire 4005 is pulled toward the distal end, and the first angle wire 4005 is maintained so as to be hung on the first circular arc portion 3405.

In this way, when the tilt input portion 1905 is tilted in the up direction, the curved portion 605 is curved in the down direction. When the tilt input portion 1905 is tilted in the down direction, the curved portion 605 is curved in the up direction.

Further, when the tilt input portion 1905 is tilted in the left direction L, the swinging member 2405 rotates in the clockwise direction (the direction Q1 shown in FIG. 14) about the second tilt axis O2 when seen along the second tilt axis O2 from the first circular arc portion 3405 toward the second circular arc portion 3605. Accordingly, the first angle wire 4005 which is hung on the first circular arc portion 3405 and the second angle wire 4105 which is hung on the second circular arc portion 3605 respectively engage with the first circular arc portion 3405 and the second circular arc portion 3605 through friction therebetween, and move along the first circular arc portion 3405 and the second circular arc portion 3605 in the direction Q1. At this time, in the curved portion 605, the ends fixed to right side in the distal end node ring member 1205A are respectively pulled between both ends of each of the first angle wire 4005 and the second angle wire 4105. Then, the right side of the distal end node ring member 1205A is pulled toward the proximal end by the first angle wire 4005 and the second angle wire 4105, and the curved portion 605 is curved in the right direction (in FIG. 14, the side indicated by the reference sign r). Further, when the curved portion 605 is curved in the right direction, the first angle wire 4005 and the second angle wire 4105 fixed to the left side of the distal end node ring member 1205A are pulled toward the distal end, and the first angle wire 4005 and the second angle wire 4105 are maintained so as to be hung on the first circular arc portion 3405 and the second circular arc portion 3605.

On the contrary, when the tilt input portion 1905 is tilted in the right direction R, the swinging member 2405 rotates in the opposite direction (the direction Q2 shown in FIG. 14) from the direction Y1. Accordingly, the first angle wire 4005 which is hung on the first circular arc portion 3405 and the second angle wire 4105 which is hung on the second circular arc portion 3605 respectively engage with the first circular arc portion 3405 and the second circular arc portion 3605 through friction therebetween, and move along the first circular arc portion 3405 and the second circular arc portion 3605 in the direction Q2. At this time, in the manner opposite to the case where the tilt input portion 1905 is tilted in the left direction L, in the curved portion 605, the ends fixed to the left side in the distal end node ring member 1205A are respectively pulled between both ends of each of the first angle wire 4005 and the second angle wire 4105. Then, the left side of the distal end node ring member 1205A is pulled toward the proximal end by the first angle wire 4005 and the second angle wire 4105, and the curved portion 605 is curved in the left direction (in FIG. 14, the side indicated by the reference sign l). Further, when the curved portion 605 is curved in the left direction, the first angle wire 4005 and the second angle wire 4105 fixed to the right side of the distal end node ring member 1205A are pulled toward the distal end, and the first angle wire 4005 and the second angle wire 4105 are maintained so as to be hung on the first circular arc portion 3405 and the second circular arc portion 3605.

In this way, when the tilt input portion 1905 is tilted in the left direction, the curved portion 605 is curved in the right direction. When the tilt input portion 1905 is tilted in the right direction, the curved portion 605 is curved in the left direction.

From the above, when the tilt input portion 1905 is tilted, the curved portion 605 is curved in the direction opposite to the side to which the proximal end of the tilt input portion 1905 is moved. Furthermore, the tilt input portion 1905 may be tilted by the appropriate combinations of the up direction, the down direction, the left direction, and the right direction. That is, the tilt input portion 1905 may be tilted in the up-left direction, the up-right direction, the down-left direction, and the down-right direction. Accordingly, the curved portion 605 may be curved in the up-left direction, the up-right direction, the down-left direction, and the down-right direction.

Conventionally, it is general to arrange four angle wires away from each other by 90° in the circumferential direction of the curved portion which may be curved upward, downward, leftward, and rightward in the endoscope apparatus.

Further, it is common in the art to arrange four angle wires with the same positional relationship inside the flexible portion. On the other hand, the angle wires away from each other by 90° in the curved portion of the endoscope apparatus may be offset from each other by 45° as disclosed in Japanese Patent Application, First Publication No. 2000-23908. In this case, when the angle wires have an offset different from the positional relationship in which the angle wires are away from each other by 90° in the circumferential direction of the curved portion, the pulling amount of the angle wire and the curved amount of the curved portion are different for each angle wire. Accordingly, the operation amount of the operation section and the curved amount of the curved portion may be different for each curving direction, and the sense of operation may be degraded.

On the contrary, according to the endoscope apparatus 105 that includes the operation section 305 provided with the operation mechanism 405 of the embodiment, the relationship of the diameter A of the first circular arc portion 3405, the diameter C of the second circular arc portion 3605, and the distance B between the first circular arc portion 3405 and the second circular arc portion 3605 with respect to the distance a between both ends of the first angle wire 4005 fixed to the distal end node ring member 1205A, the distance c between both ends of the second angle wire 4105 fixed to the distal end node ring member 1205A, and the distance b between the first angle wire 4005 and the second angle wire 4105 of the distal end node ring member 1205A are set so that distance a:distance b=distance A:diameter B and distance a:distance c=diameter A:diameter C. Accordingly, even when the first angle wire 4005 and the second angle wire 4105 of the curved portion 605 are arranged except for the arrangement in which the first and second angle wires are away from each other by 90° in the circumferential direction of the curved portion 605, the angle at which the tilt input portion 1905 is tilted and the angle at which the curved portion 605 is curved may be made to be equal to each other regardless of the direction in which the tilt input portion 1905 is tilted. As a result, the degree in freedom of the arrangement of the first angle wire 4005 and the second angle wire 4105 in the curved portion 605 and the flexible portion 705 may be improved without degrading the sense of operation of the operation section 305.

Further, since the degree of freedom in the arrangement of the first angle wire 4005 and the second angle wire 4105 inside the curved portion 605 and the flexible portion 705 may be improved, the curved portion 605 and the flexible portion 705 may be further decreased in diameter.

Further, since the swinging member 2405 is formed in a substantially spherical shape which has a sphere center on the first tilt axis O1, the first angle wire 4005 and the second angle wire 4105 may be pulled by swinging the swinging member 2405 about the sphere center.

Further, since the swinging member 2405 is provided with the first wire guide 3205 and the second wire guide 3305 which are respectively formed in a disk shape and have a cylindrical surface shaped outer peripheral surface, the first angle wire 4005 and the second angle wire 4105 are supported by the respective outer peripheral surfaces of the first wire guide 3205 and the second wire guide 3305. Accordingly, the first angle wire 4005 and the second angle wire 4105 can be suppressed from being separated from the swinging member 2405.

Further, since the first wire guide 3205 and the second wire guide 3305 are formed in a disk shape and have the same diameter as the diameter of each of the first circular arc portion 3405 and the second circular arc portion 3605, the sense of operation when pulling the first angle wire 4005 and the second angle wire 4105 may be made to be the same as the sense of operation of pulling the wires along the outer periphery of the pulley.

Further, since the first circular arc portion 3405 and the second circular arc portion 3605 are respectively provided in the swinging member 2405 and the first circular arc portion 3405 and the second circular arc portion 3605 face each other with the sphere center of the swinging member 2405 interposed therebetween, when one of the first circular arc portion 3405 and the second circular arc portion 3605 moves toward the distal end, the other of the first circular arc portion 3405 and the second circular arc portion 3605 moves toward the proximal end. Accordingly, even the curved portion 605 is curved, the first angle wire 4005 and the second angle wire 4105 can be suppressed from being bent and buckled.

Next, the configuration of the modified example of the operation mechanism 405 of the embodiment will be described.

Figure 16:
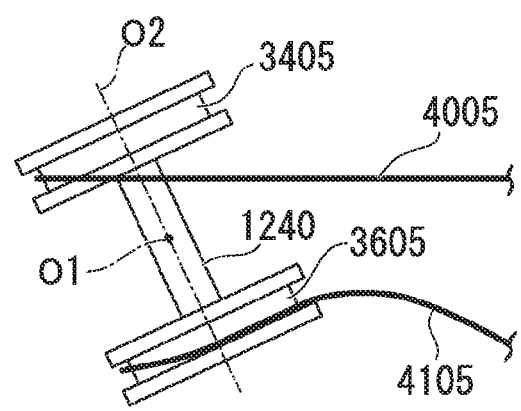
FIG. 16 is a side view illustrating the configuration of a part of an operation mechanism of a first modified example of the embodiment.

FIG. 16 is a side view illustrating the configuration of a part of the operation mechanism of the modified example.

As shown in FIG. 16, this modified example is different from the configuration of the operation mechanism 405 of the above-described embodiment in that a swinging member 1240 is provided instead of the swinging member 2405.

As not in the swinging member 2405 of the first embodiment formed in a substantially spherical shape, the swinging member 1240 is formed in a columnar shape in which the second tilt axis O2 becomes the center axis line. Further, both ends of the cylindrical portion of the swinging member 1240 in the center axis line direction are provided with the first circular arc portion 3405 and the second circular arc portion 3605 described above. In this modified example, the first wire guide 3205 and the second wire guide 3305 described above are not provided. Further, grooves are provided in the outer peripheral surfaces of the first circular arc portion 3405 and the second circular arc portion 3605 to which the first angle wire 4005 and the second angle wire 4105 are respectively fitted so that the first angle wire 4005 and the second angle wire 4105 which are respectively hung on the first circular arc portion 3405 and the second circular arc portion 3605 are not separated from the first circular arc portion 3405 and the second circular arc portion 3605.

Even in such a configuration, the same effect as that of the above-described embodiment may be obtained.

Next, the configuration of another modified example of the operation mechanism 405 of the embodiment will be described.

Figure 17:
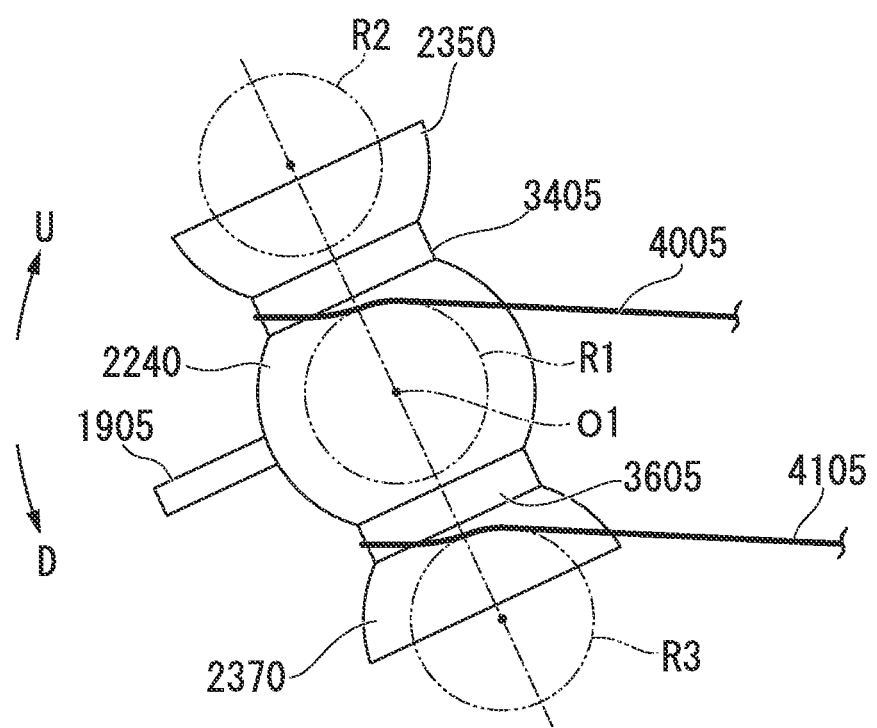
FIG. 17 is a side view illustrating the configuration of a part of an operation mechanism of a second modified example of the embodiment.

FIG. 17 is a side view illustrating the configuration of a part of the operation mechanism of the modified example.

As shown in FIG. 17, the modified example is different from the configuration of the operation mechanism 405 of the above-described embodiment in that a swinging member 2240 is provided instead of the swinging member 2405.

The swinging member 2240 of this modified example is formed in a substantially spherical shape, and includes a substantially semi-spherical third wire guide 2350 which is formed at the opposite side of the sphere center of the swinging member 2240 with the first circular arc portion 3405 interposed therebetween and a substantially semi-spherical fourth wire guide 2370 which is formed at the opposite side of the sphere center of the swinging member 2240 with the second circular arc portion 3605 interposed therebetween. The swinging member 2240 does not include the first wire guide 3205 and the second wire guide 3305 described above, but the outer surface of the sphere of the swinging member 2240 has the same function as those of the first wire guide 3205 and the second wire guide 3305. Specifically, in the outer surface of the sphere of the swinging member 2240, in the portion of the circumference R1 of which the center is positioned on the first tilt axis O1 and has the same diameter as those of the first circular arc portion 3405 and the second circular arc portion 3605, the outer surface of the spherical body of the swinging member 2240 respectively support the first angle wire 4005 and the second angle wire 4105. Furthermore, the circumference R1 is set at both sides of the swinging member 2240 in the first tilt axis O1 direction.

In the embodiment, the outer surface closer to the first circular arc portion 3405 than the sphere center of the substantially spherical swinging member 2240 is a curved surface portion which supports the first angle wire 4005, and the outer surface closer to the second circular arc portion 3605 than the sphere center of the swinging member 2240 is a second curved surface portion which supports the second angle wire 4105.

The third wire guide 2350 forms a part of the curved surface which is convex in the direction opposite to the above-described curved surface portion as a part of the spherical surface having the same diameter as the diameter of the sphere of the swinging member 2240 on the side close to the sphere center of the swinging member 2240. In the third wire guide 2350, the circumference R2 having the same diameter as that of the above-described circumference R1 is set in order to support the first angle wire 4005.

The fourth wire guide 2370 forms a part of the curved surface which is convex in the direction opposite to the above-described second curved surface portion as a part of the spherical surface having the same diameter as the diameter of the sphere of the swinging member 2240 on the side close to the sphere center of the swinging member 2240. In the fourth wire guide 2370, the circumference R3 having the same diameter as that of the above-described circumference R1 is set in order to support the second angle wire 4105.

In this modified example, when the tilt input member 1905 is tilted to the downside (in FIG. 17, the side indicated by the reference sign D), the first circular arc portion 3405 rotates about the first rotation axis O1 and moves toward the proximal end. Then, the first angle wire 4005 which is hung on the first circular arc portion 3405 is supported on the circumference R1 on the outer surface of the sphere of the swinging member 2240.

Further, at this time, the second circular arc portion 3605 rotates about the first rotation axis O1 and moves toward the distal end. Then, the second angle wire 4105 which is hung on the second circular arc portion 3605 is supported by the fourth wire guide 2370 on the circumference R3 of the outer surface of the fourth wire guide 2370.

On the contrary, when the tilt input member 1905 is tilted to the upside (in FIG. 17, the side indicated by the reference sign U), the second circular arc portion 3605 rotates about the first rotation axis O1 and moves toward the proximal end. Then, the second angle wire 4105 which is hung on the second circular arc portion 3605 is supported on the circumference R1 on the outer surface of the sphere of the swinging member 2240.

Further, at this time, the first circular arc portion 3405 rotates about the first rotation axis O1 and moves toward the distal end. Then, the first angle wire 4005 which is hung on the first circular arc portion 3405 is supported by the third wire guide (the second facing curved surface portion) 2350 on the circumference R2 of the outer surface of the third wire guide (the facing curved surface portion) 2350.

In this way, even in this modified example, the same effect as that of the above-described embodiments can be obtained. Further, the third wire guide 2350 and the fourth wire guide 2370 protrude outward in the radial direction in relation to the first circular arc portion 3405 and the second circular arc portion 3605, and form a part of the spherical surface. Accordingly, the first angle wire 4005 and the second angle wire 4105 are not easily separated from the first circular arc portion 3405 and the second circular arc portion 3605.

Further, when the first angle wire 4005 and the second angle wire 4105 are pulled toward the proximal end, the first angle wire 4005 or the second angle wire 4105 is pulled while being supported along the circumference R2 of the third wire guide 2350 and the circumference R3 of the fourth wire guide 2370. Accordingly, the sense of operation when pulling the first angle wire 4005 and the second angle wire 4105 may be made to be the same as the sense of operation when pulling the wire along the outer periphery of the pulley.

While the preferred embodiment of the invention has been described, the invention is not limited to the embodiment. Additions, omissions, substitutions, and other modifications of the configuration may be made without departing from the scope of the invention.

For example, a coating (not shown) which is formed of polytetrafluoroethylene (PTFE) may be performed on the outer peripheral surfaces of the first angle wire 4005 and the second angle wire 4105 as a coating which improves a sliding property. In this case, it is possible to reduce a friction resistance in the outer peripheral surfaces of the first angle wire 4005 and the second angle wire 4105, and efficiently transmit a force which is applied to the wire to the curved portion. Further, in the outer peripheral surfaces of the first angle wire 4005 and the second angle wire 4105, defric coat, silicone oil, or the like may be used instead of PTFE.

Furthermore, for the purpose of suppressing the sliding between the first circular arc portion 3405 and the first angle wire 4005 and the sliding between the second circular arc portion 3605 and the second angle wire 4105, the first angle wire 4005 and the second angle wire 4105 may be formed as a stranded cable. At the same time, the outer peripheral surface of each of the first circular arc portion 3405 and the second circular arc portion 3605 may have an uneven shape which engages with the stranded shape of the stranded cable. Further, for the same purpose, the respective portions of the first angle wire 4005 and the second angle wire 4105 which engage with the first circular arc portion 3405 and the second circular arc portion 3605 may be formed as a chain. At the same time, the outer peripheral surface of each of the first circular arc portion 3405 and the second circular arc portion 3605 may be provided with an uneven portion formed by transferring of a chain shape. When such a shape is formed, the first angle wire 4005 is hung on the outer peripheral surface of the first circular arc portion 3405, and the second angle wire 4105 is hung on the outer peripheral surface of the second circular arc portion 3605, thereby suppressing the slipping.

Further, the materials of the first angle wire 4005 and the second angle wire 4105 are not limited to stainless steel. For example, the first angle wire 4005 and the second angle wire 4105 may be formed as a wire which is formed of another metal material such as nickel-titanium alloy, a so-called high tensile wire having a high strength due to a heat treatment or the like, a wire formed of a resin material, or a wire formed of a carbon fiber.

Further, in the above-described embodiment, an example has been described in which the swinging member 2405 has a substantially spherical shape, but the same effect as that of the invention may be obtained even when the swinging member is formed in any shape other than the spherical shape. For example, the shape of the outer surface of the swinging member may be formed as a curved surface that forms a part of a curved surface which is convex toward the first circular arc portion near the first circular arc portion away from the intersection point between the first tilt axis and the second tilt axis in the swinging member. At the same time, any shape other than the spherical shape may be adopted in which a curved surface forms a part of a curved surface that is convex toward the second circular arc portion near the second circular arc portion away from the intersection point.

Further, in the above-described embodiment, an example has been described in which the curved portion 605 is curved by tilting the swinging member 2405 using the operation input portion 1905, but the configuration of the operation mechanism 405 is not limited thereto. For example, the force transmitting direction may be opposite to that of the above-described embodiment. That is, an operation mechanism may be easily configured which inputs a pulling force to the distal ends of the first angle wire 4005 and the second angle wire 4105 of the above-described embodiment and changes the direction of the operation input portion 1905 by swinging the swinging member 2405 using the pulling force.

In addition, the invention is not limited to the above-described embodiment, and is limited only to the appended claims.

As described above, according to the embodiments of the invention, the following technical effects can be obtained.

The curved portion of the endoscope apparatus may be made to be curved and the endoscope treatment instrument may be made to protrude and rotate by using the tilt input portion and the endoscope treatment instrument attached to the tilt input portion.

Further, since the endoscope apparatus includes the tilt input portion in addition to the rotation input portion, it is possible to intuitively operate the curved portion using the tilt input portion compared to the rotation in the rotation input portion.

Further, the rotation input portion may rotate about the rotation axis O2, and the tilt input portion may tilt the operation stick within a predetermined movable range. However, since the tilt input portion includes the clutch mechanism, even when the rotation input portion rotates about the rotation axis O2, the operation stick cannot be operated if the operation stick is present at the neutral position. As a result, it is possible to suppress the useless operation of the operation stick and operate the rotation input portion regardless of the movable range of the operation stick.

Further, since the length in which the operation wire is pulled when the operation stick is tilted by a predetermined angle is shorter than the length in which the operation wire is pulled when the rotation input portion is rotated by a predetermined angle, it is possible to highly precisely perform the minute curving operation of the curved portion using the operation stick. Further, when the endoscope treatment instrument is used while being attached to the operation stick, the treatment portion of the endoscope treatment instrument may be slightly moved relative to the treatment subject portion. However, in this case, the treatment portion may be highly precisely moved relative to the treatment subject portion.

Further, since the coil spring which biases the operation stick toward the neutral position is provided, it is possible to position the operation stick in the neutral position with a simple configuration.

Further, since the operation stick is formed in a cylindrical shape and communicates with the inside of the treatment instrument channel, the operation section of the endoscope treatment instrument is inserted into the operation stick, and the operation stick may be tilted while gripping the operation section or the grip portion. As a result, it is possible to operate the endoscope treatment instrument and the endoscope apparatus by a hand opposite to the hand holding the grip portion of the endoscope apparatus and operate the operation section of the treatment instrument, which is operated by an assistant conventionally, by the operator who operates the endoscope apparatus.

When the disk member is the sprocket wheel, the sliding between the disk member and the driving wire may be suppressed. As a result, it is possible to highly precisely curve the curved portion by reliably pulling the operation wire through the driving wire.

The relationship of the diameter A of the first circular arc portion, the diameter C of the second circular arc portion, and the distance B between the first circular arc portion and the second circular arc portion with respect to the distance a between both ends of the first angle wire fixed to the distal end node ring member, the distance c between both ends of the second angle wire fixed to the distal end node ring member, and the distance b between the first angle wire and the second angle wire of the distal end node ring member are set so that distance a:distance b=distance A:diameter B and distance a:distance c=diameter A:diameter C. Accordingly, even when the first angle wire and the second angle wire of the curved portion are arranged except for the arrangement in which the first and second angle wires are away from each other by 90° in the circumferential direction of the curved portion, the angle at which the tilt input portion is tilted and the angle at which the curved portion is curved can be made to be equal to each other regardless of the direction in which the tilt input portion is tilted. As a result, the degree in freedom of the arrangement of the first angle wire and the second angle wire in the curved portion and the flexible portion can be improved without degrading the sense of operation of the operation section.

Further, since the degree of freedom in the arrangement of the first angle wire and the second angle wire inside the curved portion and the flexible portion may be improved, the curved portion and the flexible portion may be further decreased in diameter.

Further, since the swinging member is formed in a substantially spherical shape which has a sphere center on the first tilt axis O1, the first angle wire and the second angle wire may be pulled by swinging the swinging member about the sphere center.

Further, since the swinging member is provided with the first wire guide and the second wire guide which are respectively formed in a disk shape and have a cylindrical outer peripheral surface, the first angle wire and the second angle wire are supported by the respective outer peripheral surfaces of the first wire guide and the second wire guide. Accordingly, the first angle wire and the second angle wire can be suppressed from being separated from the swinging member.

Further, since the first wire guide and the second wire guide are formed in a disk shape and have the same diameter as the diameter of each of the first circular arc portion and the second circular arc portion, the sense of operation when pulling the first angle wire and the second angle wire can be made to be the same as the sense of operation of pulling the wires along the outer periphery of the pulley.

What is claimed is:

1. An endoscope apparatus comprising:
   a longitudinal member that has a longitudinal axis and has a channel through which a medical device is capable of being inserted along the longitudinal axis;
   a subject operation section that is provided at a distal end side of the longitudinal member and has a curved portion that is capable of being curved;
   an operation section main body that is provided at a proximal end side of the longitudinal member and has a hole communicating with the channel and through which the medical device is inserted, the operation section to be supported by an operator;
   a first input portion provided in the operation section main body for curving the curved portion;

a first transmission means, a distal end of which being connected to the curved portion, the first transmission means that transmits an input operation of the first input portion to the curved portion;

a second input portion to which an operation amount of an operation section of the medical device with respect to the operation section main body is transmitted, the second input portion being provided in the operation section main body so as to be capable of being tilt operated toward a predetermined direction by a tilting operation of the medical device itself with respect to the operation section main body, and supporting the medical device being inserted into the channel via the hole rotatably around the longitudinal axis and slidably along the longitudinal axis;

a driving section being provided in the operation section main body and configured to transfer a driving force for curving the curved portion corresponding to the operation amount transmitted to the second input portion; and a second transmission means that transmits the driving force transferred from the driving section to the first input portion in order to curve the curved portion.

2. The endoscope apparatus according to claim 1, wherein the first transmission means and the second transmission means include a wire-like member.

3. The endoscope apparatus according to claim 2, wherein the first input portion is a rotation input portion to which the driving force for curving the curved portion is input by rotating about the rotation axis, and the second input portion is a tilt input portion to which the driving force for curving the curved portion is input by tilting from a predetermined neutral position.

4. The endoscope apparatus according to claim 3, wherein the second transmission means includes an input wire that is connected to the first input portion and transmits the driving force input to the tilt input portion to the first input portion, and the tilt input portion includes a clutch mechanism that transmits the driving force input to the tilt input portion from the tilt input portion to the input wire so that the tilt input portion and the input wire move in a synchronized manner when the tilt input portion is tilted from the neutral position and releases the synchronized movement between the tilt input portion and the input wire when the tilt input portion is present at the neutral position.

5. The endoscope apparatus according to claim 4, wherein the tilt input portion includes a shaft-like operation stick that is connected to the clutch mechanism for pulling an operation wire that is the wire-like member in the first transmission means, and the length in which the operation wire is pulled when the operation stick is tilted by a predetermined angle is smaller than the length in which the operation wire is pulled when the rotation input portion is rotated by the predetermined angle.

6. The endoscope apparatus according to claim 5, further comprising:

a neutral mechanism that applies a biasing force to the operation stick so as to move the operation stick to the neutral position.

7. The endoscope apparatus according to claim 5, wherein the channel is a cylindrical member which extends from the tilt input portion to a distal end of an insertion section adopted to be inserted into a body cavity and into which a treatment instrument used to perform a treatment on a tissue of a living body is inserted, and wherein the operation stick is formed in a cylindrical shape that communicates with the inside of the channel.

* * * * *